United States Patent
Koley et al.

(10) Patent No.: US 11,633,466 B2
(45) Date of Patent: Apr. 25, 2023

(54) **ENTERIC FEVER VACCINE BASED ON OUTER MEMBRANE VESICLES FROM TWO DIFFERENT STRAINS OF TYPHOIDAL *SALMONELLE* SPECIES**

(71) Applicant: Indian Council of Medical Research, New Delhi (IN)

(72) Inventors: Hemanta Koley, Beliaghata-Kolkata (IN); Debaki Ranjan Howlader, Kolkata (IN); Shanta Dutta, Kolkata (IN)

(73) Assignee: INDIAN COUNCIL OF MEDICAL RESEARCH, New Delhi (IN)

( * ) Notice: Subject to any disclaimer, the term of this patent is extended or adjusted under 35 U.S.C. 154(b) by 413 days.

(21) Appl. No.: 16/494,947

(22) PCT Filed: Mar. 21, 2018

(86) PCT No.: PCT/IN2018/050158
§ 371 (c)(1),
(2) Date: Sep. 17, 2019

(87) PCT Pub. No.: WO2018/179003
PCT Pub. Date: Oct. 4, 2018

(65) Prior Publication Data
US 2020/0384095 A1    Dec. 10, 2020

(51) Int. Cl.
*A61K 39/112* (2006.01)
*A61P 31/04* (2006.01)
*A61K 39/00* (2006.01)

(52) U.S. Cl.
CPC .......... *A61K 39/0275* (2013.01); *A61P 31/04* (2018.01); *A61K 2039/52* (2013.01); *A61K 2039/57* (2013.01)

(58) Field of Classification Search
None
See application file for complete search history.

(56) References Cited

U.S. PATENT DOCUMENTS

2015/0231232 A1* 8/2015 Grandi .................... A61P 37/08
424/244.1

FOREIGN PATENT DOCUMENTS

WO    WO 2014/044728 A1    3/2014
WO    WO-2014044728 A1 *  3/2014   ............. A61P 35/00
WO    WO 2014/192031 A1   12/2014

OTHER PUBLICATIONS

Alaniz et al., Journal of Immunology, vol. 179, No. 11, 2007. (Year: 2007).*
Alaniz et al., Journal of Immunology, vol. 179, No. 11, Year 2007 . (Year: 2007).*
International Search Report issued by the International Searching Authority dated Oct. 11, 2018 in connection with International Application No. PCT/IN2018/050158.
Written Opinion of the International Searching Authority issued dated Oct. 11, 2018 in connection with the International Application No. PCT/IN2018/050158.
Alaniz R.C., et al., "Membrane vesicles are immunogenic facsimiles of *Salmonella typhimurium* that potently activate dendritic cells, prime B and T cell responses, and stimulate protective immunity in vivo", The Journal of Immunology, The American Association of Immunologist, US, vol. 179, No. 11, Dec. 2007, pp. 7692-7701.
Debaki R. Howlader et al., "Development of novel S. Typhi and Paratyphi A outer membrane vesicles based bivalent vaccine against enteric fever" PLOS ONE, vol. 13, No. 9, Sep. 2018, p. e0203631.
Howlader Debaki Ranjan et al., "A brief review on the immunological scenario and recent development status of vaccines against enteric fever", Vaccine, vol. 35, No. 47, Oct. 2017, pp. 6359-6366.
Jaewoo Bai et al., "Identification and Characterization of Outer Membrane Vesicle-Associated Proteins in *Salmonella enterica* Serovar Typhimurium", Infection and Immunity, vol. 82, No. 10, Oct. 2014, pp. 4001-4010.
Klimentová Jana et al., "Method of isolation and purification of outer membrane vesicles from gram-negative bacteria", Microbiological Research, Fischer, Jena, DE, vol. 170, Oct. 2014, pp. 1-9.
Leo Van Der Pol et al., "Outer membrane vesicles as platform vaccine technology", Biotechnology Journal, vol. 10, No. 11, Sep. 2015, pp. 1689-1706.
Ohad Gal-Mor V. et al., "Same species, different diseases: how and why typhoidal and non-typhoidal *Salmonella enterica* serovars differ", Frontiers in Microbiology, vol. 5, Aug. 2014, p. 391.
Ritam Sinha, et al., "Pentavalent outer membrane vesicles of Vibrio Cholerae induce adaptive immune response and protective efficacy in both adult and passive suckling mice models", Microbes and Infection, vol. 17, No. 3, Mar. 2015, pp. 215-227.

* cited by examiner

*Primary Examiner* — Gary B Nickol
*Assistant Examiner* — Khatol S Shahnan Shah
(74) *Attorney, Agent, or Firm* — Gary J. Gershik

(57) ABSTRACT

A novel consortium used as potent vaccine for treating of enteric fever, comprised of isolated Outer Membrane Vesicles (OMVs) taken from two different strains of typhoidal *Salmonella* species.

7 Claims, 13 Drawing Sheets

Specification includes a Sequence Listing.

EXHIBIT B
A. i. *S. Typhi-secreting OMV*
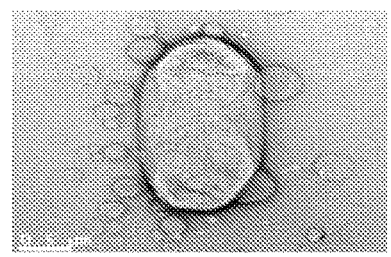
A. ii. *S. Typhi OMV*
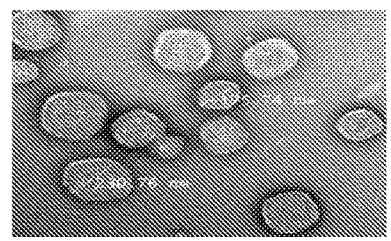
B i *S. Paratyphi A-secreting OMV*
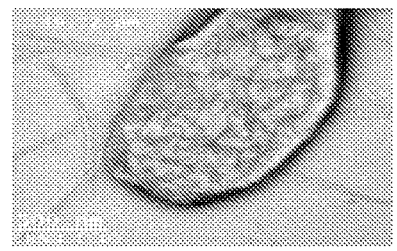
B ii *S. Paratyphi A OMV*
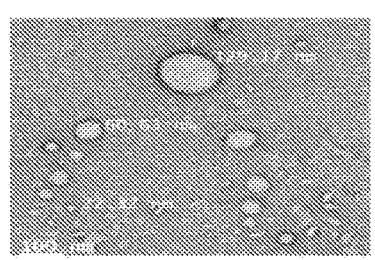
Figure 1
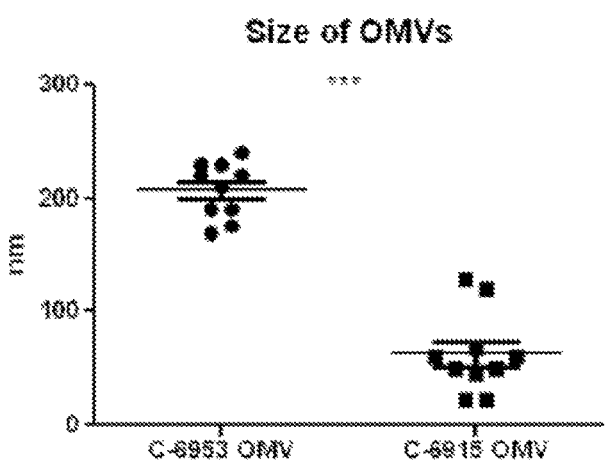
Figure : 1A

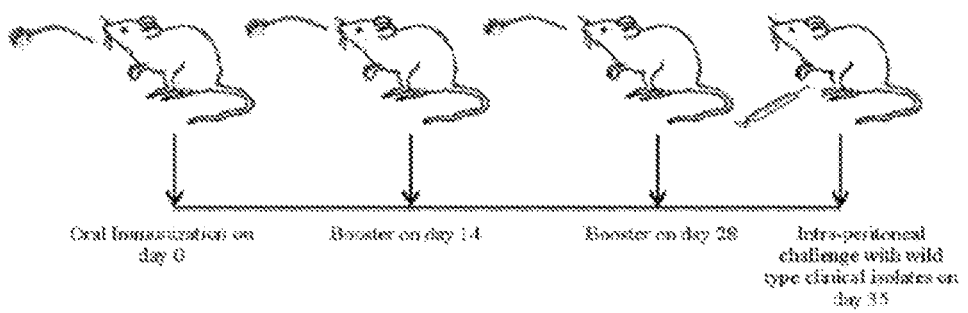
Figure : 2A
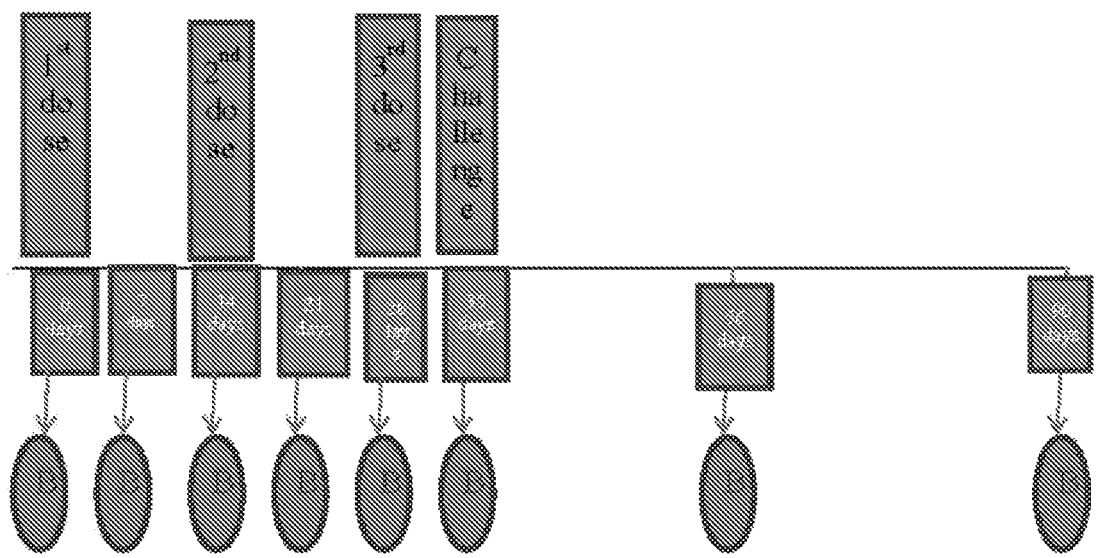
Figure 2 B

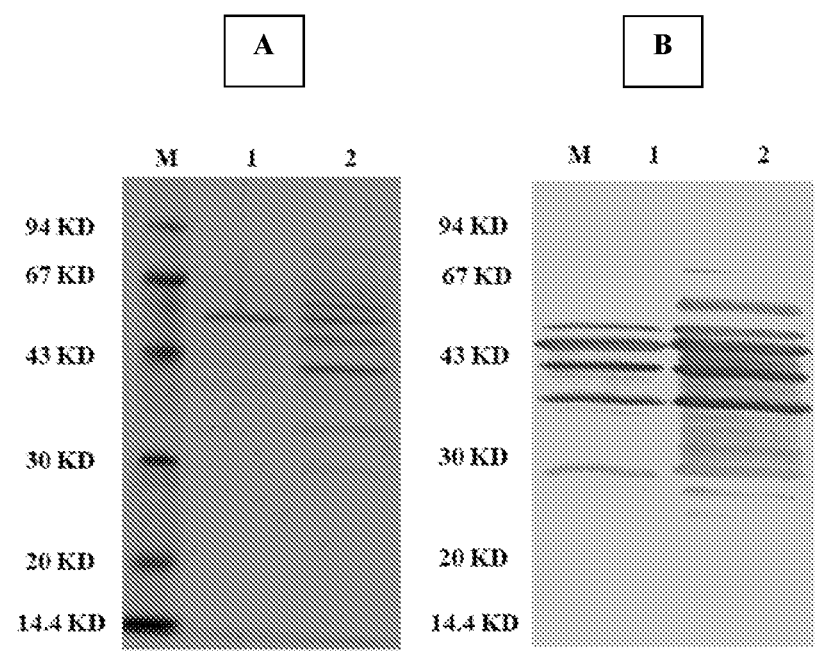
Figure 3
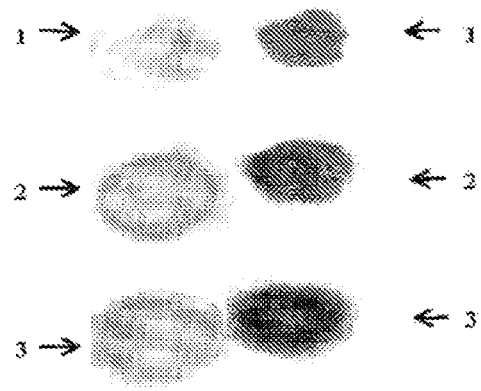
Figure : 4

A
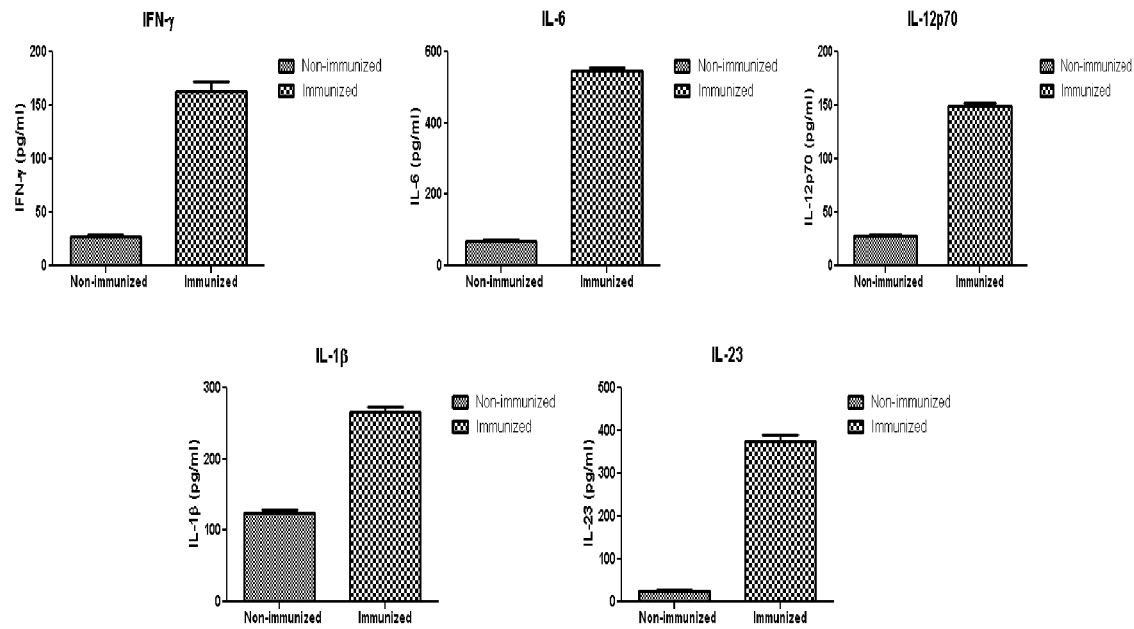
B
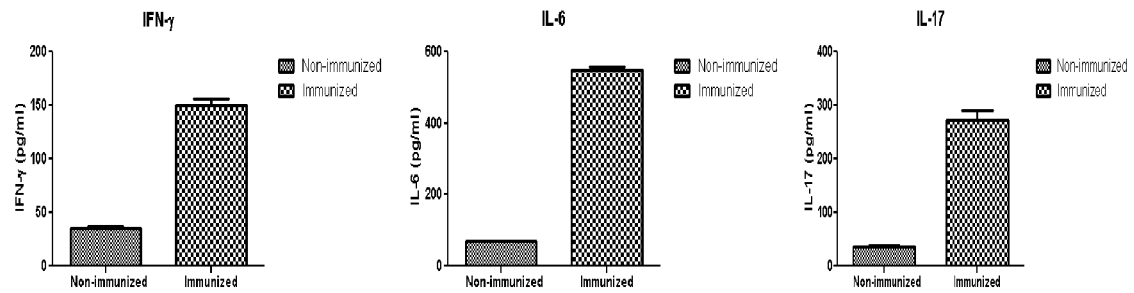
Figure 6

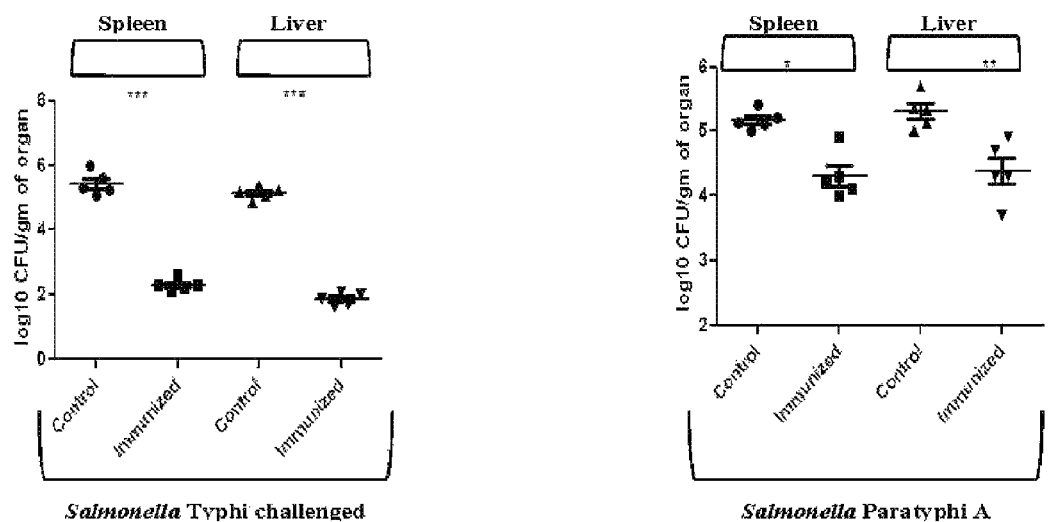
Figure : 9
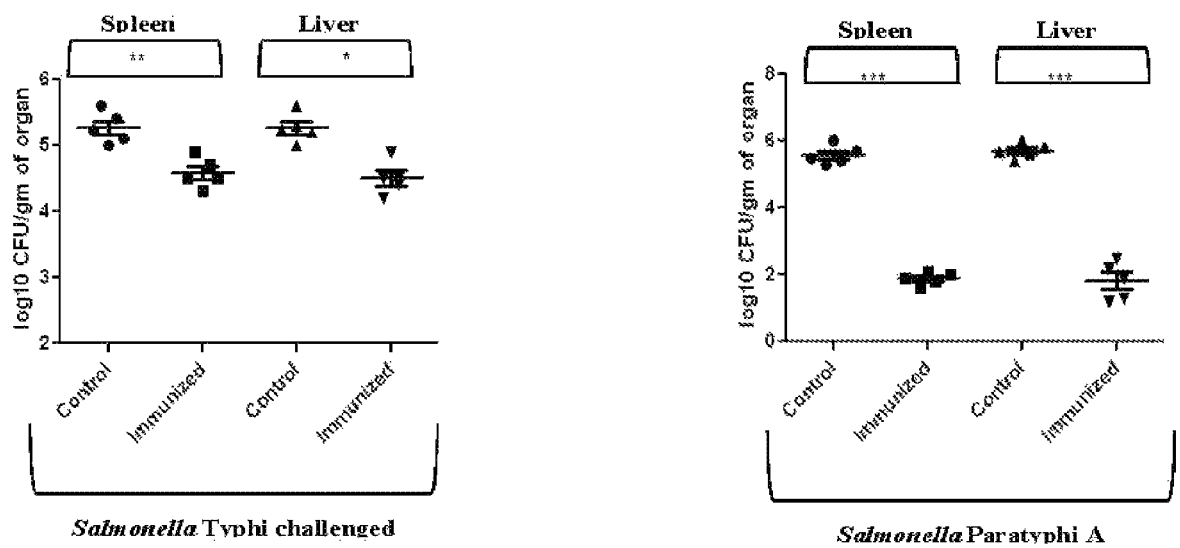
Figure : 10

SEQUENCE LISTING

```
<160> NUMBER OF SEQ ID NOS: 153

<210> SEQ ID NO 1
<211> LENGTH: 10
<212> TYPE: PRT
<213> ORGANISM: Salmonella Paratyphi A

<400> SEQUENCE: 1

Ile Ile Thr Asn Val Phe Leu Asn Ala Lys
1               5                   10

<210> SEQ ID NO 2
<211> LENGTH: 11
<212> TYPE: PRT
<213> ORGANISM: Salmonella Paratyphi A

<400> SEQUENCE: 2

Leu Thr Ala Ser Leu Leu Leu Ile Tyr Ala Lys
1               5                   10

<210> SEQ ID NO 3
<211> LENGTH: 14
<212> TYPE: PRT
<213> ORGANISM: Salmonella Paratyphi A

<400> SEQUENCE: 3

Tyr Glu Lys Asn Trp Phe Leu Pro Ile Val Thr Ile Gly Lys
1               5                   10

<210> SEQ ID NO 4
<211> LENGTH: 22
```

```
<212> TYPE: PRT
<213> ORGANISM: Salmonella Paratyphi A

<400> SEQUENCE: 4

Met Leu Thr Ala Ser

```
Ile Val Lys Lys
            20

<210> SEQ ID NO 11
<211> LENGTH: 20
<212> TYPE: PRT
<213> ORGANISM: Salmonella Paratyphi A

<400> SEQUENCE: 11

Met Ile Gln Glu Ile Leu Val Gly Ile Thr Phe Leu Ile Ala Ile Ala
1               5                   10                  15

Phe Ile Val Lys
            20

<210> SEQ ID NO 12
<211> LENGTH: 9
<212> TYPE: PRT
<213> ORGANISM: Salmonella Paratyphi A

<400> SEQUENCE: 12

Met Leu Leu Ala Leu Ala Arg Leu Lys
1               5

<210> SEQ ID NO 13
<211> LENGTH: 11
<212> TYPE: PRT
<213> ORGANISM: Salmonella Paratyphi A

<400> SEQUENCE: 13

Pro Asn Ile Leu Pro Thr Leu Pro Thr Leu Arg
1               5                   10

<210> SEQ ID NO 14
<211> LENGTH: 12
<212> TYPE: PRT
<213> ORGANISM: Salmonella Paratyphi A

<400> SEQUENCE: 14

Met Pro Asn Ile Leu Pro Thr Leu Pro Thr Leu Arg
1               5                   10

<210> SEQ ID NO 15
<211> LENGTH: 20
<212> TYPE: PRT
<213> ORGANISM: Salmonella Paratyphi A

<400> SEQUENCE: 15

Pro Asn Ile Leu Pro Thr Leu Pro Thr Leu Arg Ile Leu Pro Thr Leu
1               5                   10                  15

Pro Ile Leu Arg
            20

<210> SEQ ID NO 16
<211> LENGTH: 8
<212> TYPE: PRT
<213> ORGANISM: Salmonella Paratyphi A

<400> SEQUENCE: 16

Val Leu Val Ile Gly Asp Leu Arg
1               5

<210> SEQ ID NO 17
<211> LENGTH: 10
<212> TYPE: PRT
```

```
<213> ORGANISM: Salmonella Paratyphi A

<400> SEQUENCE: 17

Val Asp Lys Gly Ile Val Ser Le

<211> LENGTH: 10
<212> TYPE: PRT
<213> ORGANISM: Salmonella Paratyphi A

<400> SEQUENCE: 24

Asp Asp Ile Glu Ala Arg Ala Ile Ala Lys
1               5                   10

<210> SEQ ID NO 25
<211> LENGTH: 8
<212> TYPE: PRT
<213> ORGANISM: Salmonella Paratyphi A

<400> SEQUENCE: 25

Gln Ile Glu Ala Ala Lys Pro Lys
1               5

<210> SEQ ID NO 26
<211> LENGTH: 12
<212> TYPE: PRT
<213> ORGANISM: Salmonella Paratyphi A

<400> SEQUENCE: 26

Ile Leu Thr Val Gly Lys Tyr Pro Leu Met Thr Leu
1               5                   10

<210> SEQ ID NO 27
<211> LENGTH: 16
<212> TYPE: PRT
<213> ORGANISM: Salmonella Paratyphi A

<400> SEQUENCE: 27

Leu Leu Asp Gly Asn Gly Leu Tyr Leu Tyr Val Pro Val Ser Gly Lys
1               5                   10                  15

<210> SEQ ID NO 28
<211> LENGTH: 7
<212> TYPE: PRT
<213> ORGANISM: Salmonella Paratyphi A

<400> SEQUENCE: 28

Lys Phe Phe Val Thr Asp Lys
1               5

<210> SEQ ID NO 29
<211> LENGTH: 10
<212> TYPE: PRT
<213> ORGANISM: Salmonella Paratyphi A

<400> SEQUENCE: 29

Glu Ser Leu Thr Leu Glu Thr Val Leu Lys
1               5                   10

<210> SEQ ID NO 30
<211> LENGTH: 12
<212> TYPE: PRT
<213> ORGANISM: Salmonella Paratyphi A

<400> SEQUENCE: 30

Glu Ile Glu Thr Leu Leu Thr Val Gln Ala Pro Arg
1               5                   10

<210> SEQ ID NO 31
<211> LENGTH: 12
<212> TYPE: PRT

```
<213> ORGANISM: Salmonella Paratyphi A

<400> SEQUENCE: 31

Ser Glu Pro Leu Trp Arg Thr Leu Ile Gly Ile Arg
1               5                   10

<210> SEQ ID NO 32
<211> LENGTH: 13
<212> TYPE: PRT
<213> ORGANISM: Salmonella Paratyphi A

<400> SEQUENCE: 32

Asp Lys Ile Tyr Gly Ile Leu Gly Leu Leu Asn Glu Lys
1               5                   10

<210> SEQ ID NO 33
<211> LENGTH: 18
<212> TYPE: PRT
<213> ORGANISM: Salmonella Paratyphi A

<400> SEQUENCE: 33

Asp Gly Asp Thr Ile Ala Ile Ile Ala Gly Met Gly Arg Ala Ala Ile
1               5                   10                  15

Leu Arg

<210> SEQ ID NO 34
<211> LENGTH: 19
<212> TYPE: PRT
<213> ORGANISM: Salmonella Paratyphi A

<400> SEQUENCE: 34

Val Pro Ile Thr Tyr His Gly Phe Leu Met His Ser Arg Gly Thr Ile
1               5                   10                  15

His Ile Arg

<210> SEQ ID NO 35
<211> LENGTH: 24
<212> TYPE: PRT
<213> ORGANISM: Salmonella Paratyphi A

<400> SEQUENCE: 35

Gly Phe Ala Gly Val Ala Thr Pro Met Ile Arg Asp Gly Asp Thr Ile
1               5                   10                  15

Ala Ile Ile Ala Gly Met Gly Arg
            20

<210> SEQ ID NO 36
<211> LENGTH: 11
<212> TYPE: PRT
<213> ORGANISM: Salmonella Paratyphi A

<400> SEQUENCE: 36

Ala Phe Tyr Met His Leu Pro Ala Ala Gly Lys
1               5                   10

<210> SEQ ID NO 37
<211> LENGTH: 11
<212> TYPE: PRT
<213> ORGANISM: Salmonella Paratyphi A

<400> SEQUENCE: 37

Lys Leu Leu Thr Ile Leu Asn Ala Met Leu Arg
1               5                   10
```
<210> SEQ ID NO 38
<211> LENGTH: 11
<212> TYPE: PRT
<213> ORGANISM: Salmonella Paratyphi A

<400> SEQUENCE: 38

Leu Leu Thr Ile Leu Asn Ala Met Leu Arg Lys
1 5 10

<210> SEQ ID NO 39
<211> LENGTH: 25
<212> TYPE: PRT
<213> ORGANISM: Salmonella Paratyphi A

<400> SEQUENCE: 39

Met Ala Ala Leu Val Val Thr Trp Phe Asn Pro Val Ile Lys Ala Phe
1 5 10 15

Tyr Met His Leu Pro Ala Ala Gly Lys
20 25

<210> SEQ ID NO 40
<211> LENGTH: 9
<212> TYPE: PRT
<213> ORGANISM: Salmonella Paratyphi A

<400> SEQUENCE: 40

Ile Asp Trp Ile Ala Ser Gln Ile Arg
1 5

<210> SEQ ID NO 41
<211> LENGTH: 10
<212> TYPE: PRT
<213> ORGANISM: Salmonella Paratyphi A

<400> SEQUENCE: 41

Lys Ile Asp Trp Ile Ala Ser Gln Ile Arg
1 5 10

<210> SEQ ID NO 42
<211> LENGTH: 15
<212> TYPE: PRT
<213> ORGANISM: Salmonella Paratyphi A

<400> SEQUENCE: 42

Gln Leu Asn Asp Leu Leu Lys Ile Ile Phe Phe Asn Val Ile Arg
1 5 10 15

<210> SEQ ID NO 43
<211> LENGTH: 8
<212> TYPE: PRT
<213> ORGANISM: Salmonella Paratyphi A

<400> SEQUENCE: 43

Gly Ile Val Asp Pro Asp Leu Arg
1 5

<210> SEQ ID NO 44
<211> LENGTH: 9
<212> TYPE: PRT
<213> ORGANISM: Salmonella Paratyphi A

<400> SEQUENCE: 44

Met Val Glu Leu Leu Asp Leu Ile Arg 1 5

<210> SEQ ID NO 45
<211> LENGTH: 17
<212> TYPE: PRT
<213> ORGANISM: Salmonella Paratyphi A

<400> SEQUENCE: 45

Val Ala Ser Glu Ser Arg Ala Val Val Leu Gln Val Asp Ser Leu Leu
1 5 10 15

Lys

<210> SEQ ID NO 46
<211> LENGTH: 25
<212> TYPE: PRT
<213> ORGANISM: Salmonella Paratyphi A

<400> SEQUENCE: 46

Leu Leu Val Thr Val Ala Leu Ala Phe Leu Leu Val Leu Val Met Ala
1 5 10 15

Ile Phe Ser Ile Arg Ser Val Met Arg
20 25

<210> SEQ ID NO 47
<211> LENGTH: 10
<212> TYPE: PRT
<213> ORGANISM: Salmonella Paratyphi A

<400> SEQUENCE: 47

Leu Ser Ala Ser Ala Asp Leu Leu Arg Arg
1 5 10

<210> SEQ ID NO 48
<211> LENGTH: 12
<212> TYPE: PRT
<213> ORGANISM: Salmonella Paratyphi A

<400> SEQUENCE: 48

Met Leu Gln Ser Ile Phe Thr Ala Leu Leu Gly Arg
1 5 10

<210> SEQ ID NO 49
<211> LENGTH: 20
<212> TYPE: PRT
<213> ORGANISM: Salmonella Paratyphi A

<400> SEQUENCE: 49

Leu Gln Ser Ile Phe Thr Ala Leu Leu Gly Arg Leu Ser Ala Ser Ala
1 5 10 15

Asp Leu Leu Arg
20

<210> SEQ ID NO 50
<211> LENGTH: 9
<212> TYPE: PRT
<213> ORGANISM: Salmonella Paratyphi A

<400> SEQUENCE: 50

Asp Asp Glu Ile Leu Asp Leu Leu Arg
1 5

<210> SEQ ID NO 51
<211> LENGTH: 10

```
<212> TYPE: PRT
<213> ORGANISM: Salmonella Paratyphi A

<400> SEQUENCE: 51

Glu Asn G

<211> LENGTH: 11
<212> TYPE: PRT
<213> ORGANISM: Salmonella Paratyphi A

<400> SEQUENCE: 58

Gln Leu Leu Arg Asp Val Ser His Glu Leu Arg
1 5 10

<210> SEQ ID NO 59
<211> LENGTH: 13
<212> TYPE: PRT
<213> ORGANISM: Salmonella Paratyphi A

<400> SEQUENCE: 59

Leu Gln Ala Leu Ile Gly Ser Gln Arg Gln Leu Leu Arg
1 5 10

<210> SEQ ID NO 60
<211> LENGTH: 17
<212> TYPE: PRT
<213> ORGANISM: Salmonella Paratyphi A

<400> SEQUENCE: 60

Leu Pro Leu Ala Gly Pro Ala Ser Arg Thr Ser Asp Asp Leu Ala Ser
1 5 10 15

His

<210> SEQ ID NO 61
<211> LENGTH: 18
<212> TYPE: PRT
<213> ORGANISM: Salmonella Paratyphi A

<400> SEQUENCE: 61

Ala Pro Gly Gln Thr Ala Ala Gly His Gly Leu Gly Leu Ala Ile Ala
1 5 10 15

Arg Arg

<210> SEQ ID NO 62
<211> LENGTH: 35
<212> TYPE: PRT
<213> ORGANISM: Salmonella Paratyphi A

<400> SEQUENCE: 62

Asp His Gly Pro Gly Val Ala Asp Glu His Leu Pro Gln Leu Ser Glu
1 5 10 15

Pro Phe Phe Arg Ala Pro Gly Gln Thr Ala Ala Gly His Gly Leu Gly
20 25 30

Leu Ala Ile
35

<210> SEQ ID NO 63
<211> LENGTH: 10
<212> TYPE: PRT
<213> ORGANISM: Salmonella Paratyphi A

<400> SEQUENCE: 63

Tyr Phe Asp Ala Ala Arg Ser Tyr Gly Arg
1 5 10

<210> SEQ ID NO 64
<211> LENGTH: 15
<212> TYPE: PRT
<213> ORGANISM: Salmonella Paratyphi A

```
<400> SEQUENCE: 64

Val Gly Leu Ser Leu Ser Gly Pro Gln Gln Ala Ala Val Leu Arg
1               5                   10                  15

<210> SEQ ID NO 65
<211> LENGTH: 13
<212> TYPE: PRT
<213> ORGANISM: Salmonella Paratyphi A

<400> SEQUENCE: 65

Gly Met Ala Glu Ala Pro Gln Val Tyr Trp Thr Thr Arg
1               5                   10

<210> SEQ ID NO 66
<211> LENGTH: 39
<212> TYPE: PRT
<213> ORGANISM: Salmonella Paratyphi A

<400> SEQUENCE: 66

Pro His Thr Leu Gly Asn Ser Gly Pro Ala Gly Thr Ser Leu Gly Leu
1               5                   10                  15

Gly Leu Ala Ala Leu Gly Arg Pro Gly Tyr Ile Thr Leu Gly Arg Ala
            20

<210> SEQ ID NO 71
<211> LENGTH: 33
<212> TYPE: PRT
<213> ORGANISM: Salmonella Paratyphi A

<400> SEQUENCE: 71

```
Asn Asn Met Gln Gln Leu Ala Lys Pro Glu Lys Val Tyr Leu Asp Asn
1               5                   10                  15

Met Asn Leu Met Tyr Ala Leu Ser Ser Ser Ala Asp Ile Gly Asn Ile
            20                  25                  30

Arg
```

<210> SEQ ID NO 72
<211> LENGTH: 12
<212> TYPE: PRT
<213> ORGANISM: Salmonella Paratyphi A

<400> SEQUENCE: 72

```
Thr Leu Leu Asp Gly Asp Leu Gln His Arg Ile Arg
1               5                   10
```

<210> SEQ ID NO 73
<211> LENGTH: 18
<212> TYPE: PRT
<213> ORGANISM: Salmonella Paratyphi A

<400> SEQUENCE: 73

```
Ala Thr Asn Asn Leu Ala Ala Thr Thr Glu Ala Val Ala Ala Gly Ala
1               5                   10                  15

Asp Arg
```

<210> SEQ ID NO 74
<211> LENGTH: 20
<212> TYPE: PRT
<213> ORGANISM: Salmonella Paratyphi A

<400> SEQUENCE: 74

```
Asp Pro Leu Gly Gly Pro Gly Lys Pro Val Trp Ala Glu Val Val Ser
1               5                   10                  15

Val Trp Ala Lys
            20
```

<210> SEQ ID NO 75
<211> LENGTH: 38
<212> TYPE: PRT
<213> ORGANISM: Salmonella Paratyphi A

<400> SEQUENCE: 75

```
Asp Pro Leu Gly Gly Pro Gly Lys Pro Val Trp Ala Glu Val Val Ser
1               5                   10                  15

Val Trp Ala Lys Ala Thr Asn Asn Leu Ala Ala Thr Thr Glu Ala Val
            20                  25                  30

Ala Ala Gly Ala Asp Arg
        35
```

<210> SEQ ID NO 76
<211> LENGTH: 10
<212> TYPE: PRT
<213> ORGANISM: Salmonella Paratyphi A

<400> SEQUENCE: 76

```
Leu Gly Val Ser Val Ala Thr Ile Glu Arg
1               5                   10

<210> SEQ ID NO 77
<211> LENGTH: 12
<212> TYPE: PRT
<213> ORGANISM: Salmonella Paratyphi A

<400> SEQUENCE: 77

Ala Val Leu Ile Glu Ala Ile Glu Gln Ile Asp Arg
1               5                   10

<210> SEQ ID NO 78
<211> LENGTH: 19
<212> TYPE: PRT
<213> ORGANISM: Salmonella Paratyphi A

<400> SEQUENCE: 78

Leu Thr Tyr Pro Glu Ile Ala Leu Arg Leu Gly Val Ser Val Ala Thr
1               5                   10                  15

Ile Glu Arg

<210> SEQ ID NO 79
<211> LENGTH: 22
<212> TYPE: PRT
<213> ORGANISM: Salmonella Paratyphi A

<400> SEQUENCE: 79

Leu Pro Ser Arg Ala Asp Ala Glu Asp Val Thr Ser Glu Thr Phe Ala
1               5                   10                  15

Gln Val Val Glu Asn Lys
                20

<210> SEQ ID NO 80
<211> LENGTH: 32
<212> TYPE: PRT
<213> ORGANISM: Salmonella Pa -continued
<210> SEQ ID NO 83
<211> LENGTH: 12
<212> TYPE: PRT
<213> ORGANISM: Salmonella Paratyphi A

<400> SEQUENCE: 83

Leu Met Val Val Val Glu Arg Tyr Pro Glu Leu Lys
1               5                   10

<210> SEQ ID NO 84
<211> LENGTH: 8
<212> TYPE: PRT
<213> ORGANISM: Salmonella Paratyphi A

<400> SEQUENCE: 84

Gly Ile Val Asp Pro Asp Leu Arg
1               5

<210> SEQ ID NO 85
<211> LENGTH: 9
<212> TYPE: PRT
<213> ORGANISM: Salmonella Paratyphi A

<400> SEQUENCE: 85

Met Val Glu Leu Leu Asp Leu Ile Arg
1               5

<210> SEQ ID NO 86
<211> LENGTH: 17
<212> TYPE: PRT
<213> ORGANISM: Salmonella Paratyphi A

<400> SEQUENCE: 86

Val Ser Arg Gly Ile Val Ala Leu Ser Asn Gly Met Asn Ala Leu Ala
1               5                   10                  15

Lys

<210> SEQ ID NO 87
<211> LENGTH: 25
<212> TYPE: PRT
<213> ORGANISM: Salmonella Paratyphi A

<400> SEQUENCE: 87

Leu Leu Val Thr Val Ala Leu Ala Phe Leu Leu Val Leu Val Met Ala
1               5                   10                  15

Ile Phe Ser Ile Arg Ser Val Met Arg
            20                  25

<210> SEQ ID NO 88
<211> LENGTH: 11
<212> TYPE: PRT
<213> ORGANISM: Salmonella Paratyphi A

<400> SEQUENCE: 88

Ile Leu Ser Thr Thr Val Pro Val Tyr Gly Arg
1               5                   10

<210> SEQ ID NO 89
<211> LENGTH: 11
<212> TYPE: PRT
<213> ORGANISM: Salmonella Paratyphi A

<400> SEQUENCE: 89

Gln Gly Val Phe Lys Met Ser Tyr His Ile Arg 1 5 10

<210> SEQ ID NO 90
<211> LENGTH: 16
<212> TYPE: PRT
<213> ORGANISM: Salmonella Paratyphi A

<400> SEQUENCE: 90

Arg Ile Ala Tyr Asp Val His Gly Gln Ala Leu Tyr Ala Ile Ser Arg
1 5 10 15

<210> SEQ ID NO 91
<211> LENGTH: 24
<212> TYPE: PRT
<213> ORGANISM: Salmonella Paratyphi A

<400> SEQUENCE: 91

Ile Val Glu Phe Phe Glu Lys Asn Phe Pro Gly Ile Thr Pro Asp Leu
1 5 10 15

Ile Pro Thr Asp Asn Leu Gln Lys
20

<210> SEQ ID NO 92
<211> LENGTH: 31
<212> TYPE: PRT
<213> ORGANISM: Salmonella Paratyphi A

<400> SEQUENCE: 92

Asp Asn Leu Ser Leu Ser Tyr Ala Met Gln Gln Lys Glu Leu Pro Asp
1 5 10 15

Thr Pro Gln Ala Ile Val Glu Asp Tyr Leu Glu Gln Tyr Thr Lys
20 25 30

<210> SEQ ID NO 93
<211> LENGTH: 8
<212> TYPE: PRT
<213> ORGANISM: Salmonella Paratyphi A

<400> SEQUENCE: 93

His Thr Val Thr Ala Leu Ser Arg
1 5

<210> SEQ ID NO 94
<211> LENGTH: 23
<212> TYPE: PRT
<213> ORGANISM: Salmonella Paratyphi A

<400> SEQUENCE: 94

Val Ala Ile Val Gly Ala Gly Gly Thr Val Gly Ser Phe Leu Ala Ala
1 5 10 15

Ala Leu Leu Lys Thr Gly Lys
20

<210> SEQ ID NO 95
<211> LENGTH: 34
<212> TYPE: PRT
<213> ORGANISM: Salmonella Paratyphi A

<400> SEQUENCE: 95

Ala Gly Val Pro Tyr Ile Met Pro Asn Gly Tyr Ala Gly Asp Ile Glu
1 5 10 15

His Val Lys Phe Gly Gln Asp Val Met Leu Gly Pro Val Ala Gln Ala
20 25 30

Asn Arg

<210> SEQ ID NO 96
<211> LENGTH: 17
<212> TYPE: PRT
<213> ORGANISM: Salmonella Paratyphi A

<400> SEQUENCE: 96

Met Phe Ala Glu Thr Val Ile Gly Ala Pro His Gly Ile Leu Val Ser
1               5                   10                  15

Arg

<210> SEQ ID NO 97
<211> LENGTH: 25
<212> TYPE: PRT
<213> ORGANISM: Salmonella Paratyphi A

<400> SEQUENCE: 97

Phe Ala Glu Thr Val Ile Gly Ala Pro His Gly Ile Leu Val Ser Arg
1               5                   10                  15

Ile Thr Val Tyr Leu Ser Asn Ala Lys
            20                  25

<210> SEQ ID NO 98
<211> LENGTH: 26
<212> TYPE: PRT
<213> ORGANISM: Salmonella Paratyphi A

<400> SEQUENCE: 98

Met Phe Ala Glu Thr Val Ile Gly Ala Pro His Gly Ile Leu Val Ser
1               5                   10                  15

Arg Ile Thr Val Tyr Leu Ser Asn Ala Lys
            20                  25

<210> SEQ ID NO 99
<211> LENGTH: 19
<212> TYPE: PRT
<213> ORGANISM: Salmonella Paratyphi A

<400> SEQUENCE: 99

Ile Gln Glu Ile Leu Val Gly Ile Thr Phe Leu Ile Ala Ile Ala Phe
1               5                   10                  15

Ile Val Lys

<210> SEQ ID NO 100
<211> LENGTH: 8
<212> TYPE: PRT
<213> ORGANISM: Salmonella Paratyphi A

<400> SEQUENCE: 100

Arg Gly Gln Pro Ala Leu Ser Arg
1               5

<210> SEQ ID NO 101
<211> LENGTH: 8
<212> TYPE: PRT
<213> ORGANISM: Salmonella Paratyphi A

<400> SEQUENCE: 101

Gly Gln Pro Ala Leu Ser Arg Arg
1               5

```
<210> SEQ ID NO 102
<211> LENGTH: 10
<212> TYPE: PRT
<213> ORGANISM: Salmonella Paratyphi A

<400> SEQUENCE: 102

Cys Arg Leu Gln Gln Ala Thr Leu Thr Asp
1 5 10

<210> SEQ ID NO 103
<211> LENGTH: 10
<212> TYPE: PRT
<213> ORGANISM: Salmonella Paratyphi A

<400> SEQUENCE: 103

Leu Val Ile Thr Leu Arg Asp Tyr Gly Arg
1 5 10

<210> SEQ ID NO 104
<211> LENGTH: 16
<212> TYPE: PRT
<213> ORGANISM: Salmonella Paratyphi A

<400> SEQUENCE: 104

Leu Asp Cys Thr Glu Gly Leu Asp Tyr Cys Cys Ile Cys Cys Pro Lys
1 5 10 15

<210> SEQ ID NO 105
<211> LENGTH: 22
<212> TYPE: PRT
<213> ORGANISM: Salmonella Paratyphi A

<400> SEQUENCE: 105

Met Ile Gly His Cys Lys Leu Asp Cys Thr Glu Gly Leu Asp Tyr Cys
1 5 10 15

Cys Ile Cys Cys Pro Lys
20

<210> SEQ ID NO 106
<211> LENGTH: 22
<212> TYPE: PRT
<213> ORGANISM: Salmonella Paratyphi A

<400> SEQUENCE: 106

Trp Gln His Leu Ile Asn Asp Leu Gln Asn Asp Arg Ser Val Asp Asp
1 5 10 15

Glu Pro Gly Thr Tyr Arg
20

<210> SEQ ID NO 107
<211> LENGTH: 24
<212> TYPE: PRT
<213> ORGANISM: Salmonella Paratyphi A

<400> SEQUENCE: 107

Met Ser Glu Gln Leu His Gly Asn Met His Tyr Leu Leu Thr Ser Glu
1 5 10 15

Thr Tyr Asn Gly Ile Leu Val Arg
20

<210> SEQ ID NO 108
<211> LENGTH: 17
<212> TYPE: PRT

<213> ORGANISM: Salmonella Paratyphi A

<400> SEQUENCE: 108

Met Asp Glu Trp Met Asp Gly Arg Gln Ser Leu Ala Glu Glu Thr Ser
1 5 10 15

Met

<210> SEQ ID NO 109
<211> LENGTH: 24
<212> TYPE: PRT
<213> ORGANISM: Salmonella Paratyphi A

<400> SEQUENCE: 109

Ile Leu Ala Leu Tyr Cys Val Thr Val Met Glu Ala His Glu Ile Val
1 5 10 15

Gly Val Glu Trp Gly Met Asn Arg
20

<210> SEQ ID NO 110
<211> LENGTH: 7
<212> TYPE: PRT
<213> ORGANISM: Salmonella Paratyphi A

<400> SEQUENCE: 110

Leu Leu Leu Ile Ala His Lys
1 5

<210> SEQ ID NO 111
<211> LENGTH: 27
<212> TYPE: PRT
<213> ORGANISM: Salmonella Paratyphi A

<400> SEQUENCE: 111

His Asn Ser Thr Ser Ser Ser Thr Thr Pro Asn Gln Arg Glu Gly Gly
1 5 10 15

Pro Leu Ser Gly Ile Phe Leu Ser Phe Gly Lys
20 25

<210> SEQ ID NO 112
<211> LENGTH: 25
<212> TYPE: PRT
<213> ORGANISM: Salmonella Paratyphi A

<400> SEQUENCE: 112

Thr Ala Gly Gln Leu Ile Asn Trp Gly Met Pro Thr Leu Ala Ala Glu
1 5 10 15

Met Leu Asn Ala Leu Asp Cys Gln Arg
20 25

<210> SEQ ID NO 113
<211> LENGTH: 25
<212> TYPE: PRT
<213> ORGANISM: Salmonella Paratyphi A

<400> SEQUENCE: 113

Ile Ala Val Ser Trp Ala Met Pro Val Val Leu Thr Gln Tyr Asp Ser
1 5 10 15

Val Met Ala Thr Val Met Gly Asp Ser
20 25

<210> SEQ ID NO 114
<211> LENGTH: 24

```
<212> TYPE: PRT
<213> ORGANISM: Salmonella Paratyphi A

<400> SEQUENCE: 114

Ile Lys Glu Ala Asn Glu Ala Leu Ile Asp Ala His Asn Thr Gln Thr
1 5 10 15

Gly Met Leu Thr Glu Glu Ala Arg
20

<210> SEQ ID NO 115
<211> LENGTH: 25
<212> TYPE: PRT
<213> ORGANISM: Salmonella Paratyphi A

<400> SEQUENCE: 115

Glu Ala Asn Glu Leu Ser Met Gln Gln Thr Met Met Leu Ile Met Asn
1 5 10 15

Ala Gly Asn Ala Lys Ala Phe Ala Lys
20 25

<210> SEQ ID NO 116
<211> LENGTH: 23
<212> TYPE: PRT
<213> ORGANISM: Salmonella Paratyphi A

<400> SEQUENCE: 116

Leu Trp Tyr Cys Met Met Phe Gly Val Thr Val Ala Thr Ile Tyr Gly
1 5 10 15

Ala Ala Leu Ile Leu Met Val
20

<210> SEQ ID NO 117
<211> LENGTH: 29
<212> TYPE: PRT
<213> ORGANISM: Salmonella Paratyphi A

<400> SEQUENCE: 117

Gly Asp Pro Ser Ala Ala Val Thr Ile Ala Asp Ile Ala Met Arg Ala
1 5 10 15

His Asp Ala Gly Asp Leu Pro Glu Gly Ile Glu Gly Gly
20 25

<210> SEQ ID NO 118
<211> LENGTH: 23
<212> TYPE: PRT
<213> ORGANISM: Salmonella Paratyphi A

<400> SEQUENCE: 118

Met Asp Ile Met Ile Asn Ala Ser Phe Leu Pro His Thr Asp Pro Glu
1 5 10 15

Ala Ser Leu Ala Phe Tyr Arg
20

<210> SEQ ID NO 119
<211> LENGTH: 25
<212> TYPE: PRT
<213> ORGANISM: Salmonella Paratyphi A

<400> SEQUENCE: 119

Val Gln Ala Ser Gly Ala Glu Val Met Gln Glu Pro Thr Asp Gln Pro
1 5 10 15

Trp Gly Ala Arg Asp Cys Ala Phe Arg
```

```
20 25

<210> SEQ ID NO 120
<211> LENGTH: 29
<212> TYPE: PRT
<213> ORGANISM: Salmonella Paratyphi A

<400> SEQUENCE: 120

Tyr Arg Ser Ala Pro Gln Ala Ala Ser Ala Gly Ser Pro Thr Ser Pro
1 5 10 15

Pro Ala Ser Met Gln Pro Thr Pro Ser Thr Ser Ala Ser
20 25

<210> SEQ ID NO 121
<211> LENGTH: 22
<212> TYPE: PRT
<213> ORGANISM: Salmonella Paratyphi A

<400> SEQUENCE: 121

Glu Leu Arg Asn Ser Phe Ile Met Asp Gln Asp Asn Gln Ala Ala Phe
1 5 10 15

Ile Asn Thr His Tyr Lys
20

<210> SEQ ID NO 122
<211> LENGTH: 24
<212> TYPE: PRT
<213> ORGANISM: Salmonella Paratyphi A

<400> SEQUENCE: 122

Ser Leu His Glu Asp Thr Ile Asp Pro Ile Glu Asn Glu Ala Asp His
1 5 10 15

Leu Phe Ile Ile Arg Asn Ser Lys
20

<210> SEQ ID NO 123
<211> LENGTH: 24
<212> TYPE: PRT
<213> ORGANISM: Salmonella Paratyphi A

<400> SEQUENCE: 123

Asp Asn Val Gln Cys Ala Pro Ser Gly Lys Ala Ala Ile Thr Val Ser
1 5 10 15

Phe Val Leu Glu Met Asp Phe Arg
20

<210> SEQ ID NO 124
<211> LENGTH: 25
<212> TYPE: PRT
<213> ORGANISM: Salmonella Paratyphi A

<400> SEQUENCE: 124

Met Asn Ser Arg Pro Pro Phe Pro Ser Thr Ser Ser Pro Pro Ser Gln
1 5 10 15

Pro Ser Pro Tyr Arg Tyr Leu Gly Arg
20 25

<210> SEQ ID NO 125
<211> LENGTH: 27
<212> TYPE: PRT
<213> ORGANISM: Salmonella Paratyphi A

<400> SEQUENCE: 125
```

Gln Arg Ala Gly Ala Gly Asn Gly Glu Thr Gly Ala Ser Gly Val Gly
1               5                   10                  15

Glu Gln Gln Ala Asn Pro Leu Phe Asn Leu Lys
            20                  25

<210> SEQ ID NO 126
<211> LENGTH: 24
<212> TYPE: PRT
<213> ORGANISM: Salmonella Paratyphi A

<400> SEQUENCE: 126

Thr His Glu Glu Ala Tyr Ala Ala Ala Val Glu Glu Phe Glu Ala Asn
1               5                   10                  15

Pro Pro Gln Val Gln Arg Gly Lys
            20

<210> SEQ ID NO 127
<211> LENGTH: 25
<212> TYPE: PRT
<213> ORGANISM: Salmonella Paratyphi A

<400> SEQUENCE: 127

Gly Lys Lys Pro Leu Lys Pro Tyr Glu Gly Asp Met Pro Phe Phe Asp
1               5                   10                  15

Asn Gly Asp Gly Thr Thr Thr Phe Lys
            20                  25

<210> SEQ ID NO 128
<211> LENGTH: 24
<212> TYPE: PRT
<213> ORGANISM: Salmonella Paratyphi A

<400> SEQUENCE: 128

Leu Ile Cys Lys Ala Ser Ser Ala Gln Gly Cys Ser Pro Ser Thr Thr
1               5                   10                  15

Leu Asn Gln Asn Phe Met Gln Lys
20

<210> SEQ ID NO 129
<211> LENGTH: 26
<212> TYPE: PRT
<213> ORGANISM: Salmonella Paratyphi A

<400> SEQUENCE: 129

Ala Ser Ser Ala Gln Gly Cys Ser Pro Ser Thr Thr Leu Asn Gln Asn
1 5 10 15

Phe Met Gln Lys Gly Ile Leu Glu Cys Arg
20 25

<210> SEQ ID NO 130
<211> LENGTH: 8
<212> TYPE: PRT
<213> ORGANISM: Salmonella Paratyphi A

<400> SEQUENCE: 130

Ala Leu Leu Gly Lys Met Glu Arg
1 5

<210> SEQ ID NO 131
<211> LENGTH: 28
<212> TYPE: PRT
<213> ORGANISM: Salmonella Paratyphi A

```
<400> SEQUENCE: 131

Phe Phe Arg Gly Ser Ser Gln Gln Ser Ser Gly Asn Pro Ala Thr Asp
1               5                   10                  15

Phe Phe Thr Val Ala Ser Pro Leu Pro Ala Ala Asn
            20                  25

<210> SEQ ID NO 132
<211> LENGTH: 22
<212> TYPE: PRT
<213> ORGANISM: Salmonella Paratyphi A

<400> SEQUENCE: 132

His Ile Cys Phe Glu Ile Glu Ser Tyr Met Phe Arg Ile Ala Phe His
1               5                   10                  15

Asp Phe Phe Leu Pro Ser
            20

<210> SEQ ID NO 133
<211> LENGTH: 24
<212> TYPE: PRT
<213> ORGANISM: Salmonella Paratyphi A

<400> SEQUENCE: 133

Met Ile Leu Leu His Lys Tyr Ser Ile Pro Ala Cys Ser Cys Phe Gln
1               5                   10                  15

Asn Ile Tyr Ala Leu Asn Thr Lys
            20

<210> SEQ ID NO 134
<211> LENGTH: 24
<212> TYPE: PRT
<213> ORGANISM: Salmonella Paratyphi A

<400> SEQUENCE: 134

Met Ala Cys Val Val Ser His Gln Glu Asn Gln Asp Cys Ala Ser Leu
1               5                   10                  15

Thr Pro Glu Thr Phe Leu Pro Arg
            20

<210> SEQ ID NO 135
<211> LENGTH: 8
<212> TYPE: PRT
<213> ORGANISM: Salmonella Paratyphi A

<400> SEQUENCE: 135

Val Glu Ala Ala Arg Ser Glu Arg
1               5

<210> SEQ ID NO 136
<211> LENGTH: 25
<212> TYPE: PRT
<213> ORGANISM: Salmonella Paratyphi A

<400> SEQUENCE: 136

Met Ala Cys Ser Glu Gln Glu Gly Val Gly Ser Pro Asp Glu Ala
1               5                   10                  15

Leu Phe Ala Ser Gln Glu Gly Val Lys
            20                  25

<210> SEQ ID NO 137
<211> LENGTH: 21
```

<212> TYPE: PRT
<213> ORGANISM: Salmonella Paratyphi A

<400> SEQUENCE: 137

Asn Leu Cys Thr Gln Pro Asp Gly Gly Tyr Leu Thr Asp Glu Gly Ile
1 5 10 15

Gln Met Ala Glu Arg
20

<210> SEQ ID NO 138
<211> LENGTH: 21
<212> TYPE: PRT
<213> ORGANISM: Salmonella Paratyphi A

<400> SEQUENCE: 138

Val Asp Gly Tyr Thr Val Val Trp Asp Pro Glu Thr Asp Met Val Val
1 5 10 15

Trp Ala Gly Gly Arg
20

<210> SEQ ID NO 139
<211> LENGTH: 8
<212> TYPE: PRT
<213> ORGANISM: Salmonella Paratyphi A

<400> SEQUENCE: 139

Met Arg Ile Pro Ser Thr Gly Arg
1 5

<210> SEQ ID NO 140
<211> LENGTH: 18
<212> TYPE: PRT
<213> ORGANISM: Salmonella Paratyphi A

<400> SEQUENCE: 140

Leu Ala Val Ser Ala Val Val Leu Leu Ala Ala Leu Ser Val Gln Gly
1 5 10 15

Val Arg

<210> SEQ ID NO 141
<211> LENGTH: 8
<212> TYPE: PRT
<213> ORGANISM: Salmonella Paratyphi A

<400> SEQUENCE: 141

Met Glu Pro Ser Asn Val Leu Lys
1 5

<210> SEQ ID NO 142
<211> LENGTH: 26
<212> TYPE: PRT
<213> ORGANISM: Salmonella Paratyphi A

<400> SEQUENCE: 142

Val Ile Ala Glu Gln Glu Gly Ala Asp Ser Phe Val Cys Gln Leu Ala
1 5 10 15

Ala Trp Leu His Asp Leu Ala Asp Asp Lys
20 25

<210> SEQ ID NO 143
<211> LENGTH: 20
<212> TYPE: PRT
<213> ORGANISM: Salmonella Paratyphi A -continued

```
<400> SEQUENCE: 143

Met Gly His Met Glu Arg Ser Phe Val Ser Glu Asp Trp Ala Gly Leu
1               5                   10                  15

Ala Ser Trp Arg
            20

<210> SEQ ID NO 144
<211> LENGTH: 25
<212> TYPE: PRT
<213> ORGANISM: Salmonella Paratyphi A

<400> SEQUENCE: 144

Ser Phe Val Ser Glu Asp Trp Ala Gly Leu Ala Ser Trp Arg Cys Thr
1               5                   10                  15

Cys Thr Asp Val Asp Leu Gly Leu Arg
            20                  25

<210> SEQ ID NO 145
<211> LENGTH: 7
<212> TYPE: PRT
<213> ORGANISM: Salmonella Paratyphi A

<400> SEQUENCE: 145

Met Ala Pro Trp Glu Arg Lys
1               5

<210> SEQ ID NO 146
<211> LENGTH: 8
<212> TYPE: PRT
<213> ORGANISM: Salmonella Paratyphi A

<400> SEQUENCE: 146

Asn Ala Leu Phe Thr Pro Val Arg
1               5

<210> SEQ ID NO 147
<211> LENGTH: 21
<212> TYPE: PRT
<213> ORGANISM: Salmonella Paratyphi A

<400> SEQUENCE: 147

Gln Met Thr Ala Gly Met Ala Asp Ile Met Gly Thr Ser Gly Leu Ala
1               5                   10                  15

Trp His Gln Trp Lys
            20

<210> SEQ ID NO 148
<211> LENGTH: 7
<212> TYPE: PRT
<213> ORGANISM: Salmonella Paratyphi A

<400> SEQUENCE: 148

Met Ile Thr Gln Arg Leu Arg
1               5

<210> SEQ ID NO 149
<211> LENGTH: 27
<212> TYPE: PRT
<213> ORGANISM: Salmonella Paratyphi A

<400> SEQUENCE: 149

Met Pro Leu Ala Glu Gly Val Thr Gly Glu Gly Arg Asp Thr Gln Ser
1               5                   10                  15
```

-continued

```
1               5                   10                  15

Arg Pro Val Gly Asp Asp Leu Asp Leu Thr Arg
            20                  25

<210> SEQ ID NO 150
<211> LENGTH: 12
<212> TYPE: PRT
<213> ORGANISM: Salmonella Paratyphi A

<400> SEQUENCE: 150

Lys Ile Leu Thr Glu Asp Tyr Val Asn Leu Val Lys
1               5                   10

<210> SEQ ID NO 151
<211> LENGTH: 24
<212> TYPE: PRT
<213> ORGANISM: Salmonella Paratyphi A

<400> SEQUENCE: 151

Ser Gln Leu Asn Phe Tyr Asp Thr Ser Val Tyr Asn Phe Ile Lys Ser
1               5                   10                  15

Leu Asp Tyr Ala Glu Val Glu Arg
            20

<210> SEQ ID NO 152
<211> LENGTH: 7
<212> TYPE: PRT
<213> ORGANISM: Salmonella Paratyphi A

<400> SEQUENCE: 152

Asn Gln Cys Asn Ile Leu Arg
1               5

<210> SEQ ID NO 153
<211> LENGTH: 23
<212> TYPE: PRT
<213> ORGANISM: Salmonella Paratyphi A

<400> SEQUENCE: 153

Met Leu Phe Phe Tyr Gln Leu Pro Phe Ile Ile Pro Ile Pro Ser Met
1               5                   10                  15

Gln Gly Asn Thr Phe Ser Arg
            20
```

ENTERIC FEVER VACCINE BASED ON OUTER MEMBRANE VESICLES FROM TWO DIFFERENT STRAINS OF TYPHOIDAL *SALMONELLE* SPECIES

CROSS-REFERENCE TO RELATED APPLICATIONS

This application is a § 371 national stage of PCT International Application No. PCT/IN2018/050158, filed Mar. 21, 2018, claiming priority of Indian Patent Application No. 201711011707, filed Mar. 31, 2017, the contents of each of which are hereby incorporated by reference into this application.

REFERENCE TO A SEQUENCE LISTING

This application incorporates-by-reference nucleotide and/or amino acid sequences which are present in the file named "200203_772_91062_Sequence_Listing_SC.txt", which is 35 kilobytes in size, and which was created Feb. 3, 2020 in the IBM-PC machine format, having an operating system compatibility with MS-Windows, which is contained in the text file filed Feb. 3, 2020 as part of this application.

FIELD OF INVENTION

The present invention relates to a novel consortium for a potent vaccine for enteric fever, comprised of specific strains *Salmonella typhi* and *Salmonella paratyphi* A in equal proportion.

The Present invention also relates to a methodology for preparing the said novel consortium based on outer membrane vesicles (OMV).

BACKGROUND AND PRIOR ART OF THE INVENTION

Enteric fever, a serious invasive bacterial infection, caused by *Salmonella enterica* serovers *typhi* and *paratyphi* A (hereafter, *S. typhi* and *S. paratyphi* A, respectively) is a major global burden in developed and developing countries like India. Although *S. typhi* is more prevalent, affects 21.7 million cases and 200,000 deaths per year worldwide, *S. paratyphi* (A, B and C) can cause significant enteric fever especially in Asia as well as in travelers returning from these endemic areas (1, 2, 3). Currently, there are only two licensed vaccines are available against *S. typhi*; a live attenuated galE mutant and a Vi-polysaccharide vaccine (4). Although somewhat effective, they have their limitations such as they do not provide long-term protection in children and they do not provide significant long-term immunity in adults too.

Presently, the focus of vaccine research is on acellular vaccine because of the certain drawbacks of conventional immunogens. In this changing state of vaccine research, Outer Membrane Vesicles (OMVs) has got significant importance. Neisseria meningitis OMV based licensed vaccine is now presently available in market (5). As OMVs has got both LPS and proteins, they do not need any artificial adjuvants (6).

Though OMVs are used in drug development against various microorganisms, such methods are often expensive and complicated as most of the techniques employ infusion of different proteins from outside.

As the enteric fever is most predominant in developing countries, the cost-effectivity should be the prime concern in field of vaccine development.

Further, the conventional technology often devoid of providing substantial protection against enteric fever caused by *S. typhi* and also results some hazardous side-effects in human.

Hence, there is always a need to provide an innovative formulation by using a process based on Outer Membrane Vesicles (OMV) which are overcoming the drawbacks of the conventional practice.

The present invention meets the above-mentioned long-felt need.

OBJECTIVES OF THE INVENTION

The principal object of the present invention is to provide a simple yet effective consortium comprised of isolated Outer Membrane Vesicles (OMV) of *Salmonella typhi* and *Salmonella paratyphi* A in equal proportion.

Another objective of the present invention is to provide a consortium which is effective in treating enteric fever.

Yet another objective of the present invention is to provide a simple consortium wherein any mutation or deletion of gene has not been adopted to provide the end product.

Further objective of the present invention is to provide a simple consortium wherein the mutation or deletion of gene is not incorporated to reduce the expression of immune-dominant non-protective antigens.

Another objective of the present invention is to provide a simple consortium wherein no antibiotics or any excipients have been used.

Yet another objective of the present invention is to provide a simple consortium wherein no protective proteins is incorporated from outside.

Further objective of the present invention is to provide a simple consortium wherein only isolated OMVs of *Salmonella* strain is used, hence, it is cost-effective and environment friendly.

BRIEF DESCRIPTION OF THE ACCOMPANYING DRAWINGS

It is to be noted, however, that the appended drawings illustrate only typical embodiments of the present subject matter and are therefore not to be considered for limiting of its scope, for the invention may admit to other equally effective embodiments. The detailed description is described with reference to the accompanying figures.

Some embodiments of system or methods in accordance with embodiments of the present subject matter are now described, by way of example, and with reference to the accompanying figures, in which:

FIGS. 1 and 1*a* illustrate an electron micrograph of OMVs attached to bacteria and isolated OMVs and characterization of isolated OMVs.

FIG. 2*a* illustrates mice immunization by the consortium.

FIG. 2*b* illustrates immunization and challenge regimen in mice.

FIG. 3 illustrates a representative immunoblot analysis against OMVs, from two typhoidal strains.

FIG. 4 illustrates Dot blot analysis against extracted LPS from two typhoidal strains.

FIG. 6 illustrates BOMVs induces the production of Th1 and Th17 polarizing cytokines in Ag-presenting BMDCs and splenic cells after treatment.

FIG. 9 illustrates colonization of Salmonella typhi and paratyphi A clinical isolate in Salmonella typhi monovalent OMV immunized mice.

FIG. 10 illustrates colonization of Salmonella typhi and paratyphi A clinical isolate in Salmonella paratyphi A monovalent OMV immunized mice.

DETAILED DESCRIPTION OF THE INVENTION

Figure 5:
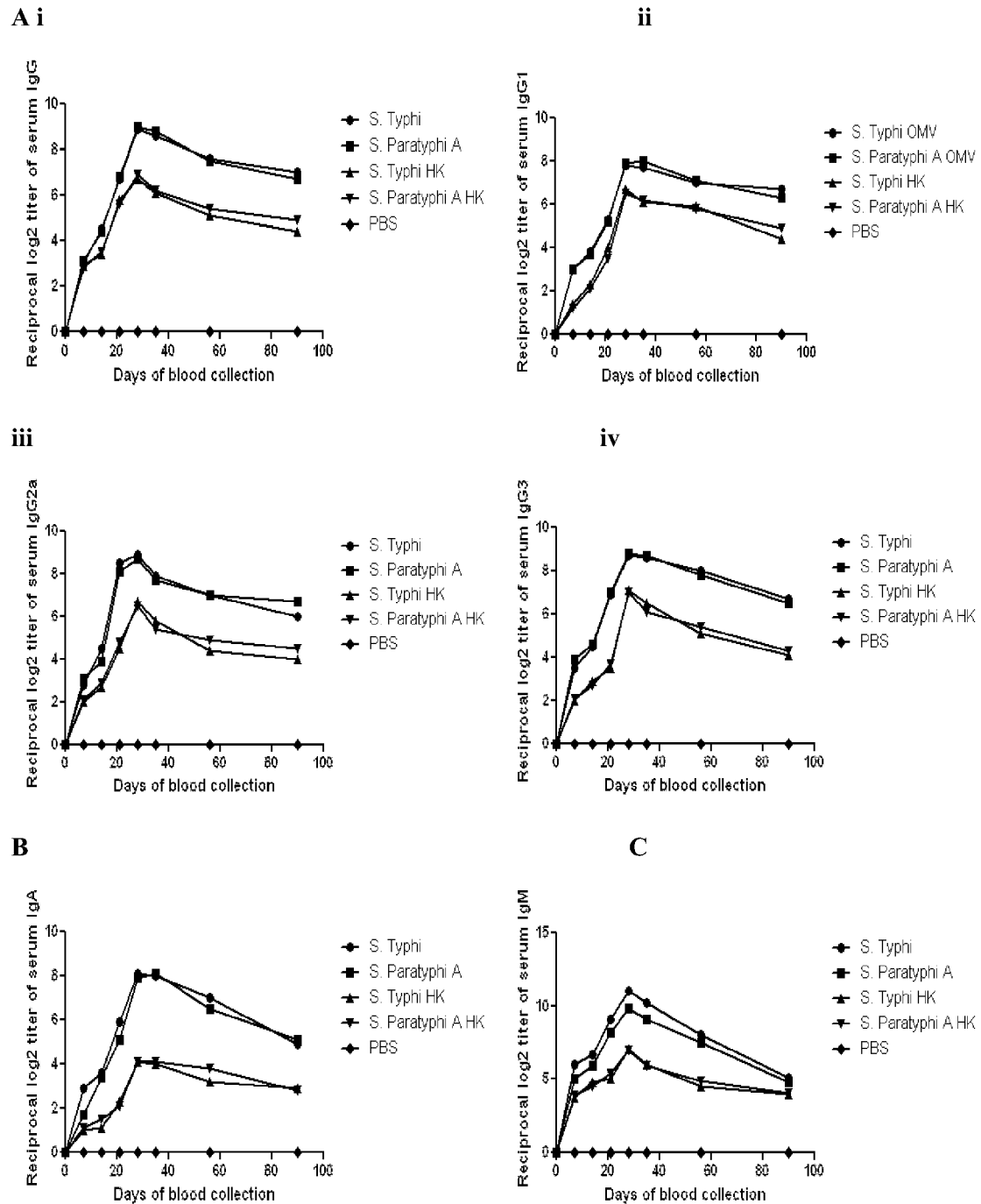
FIG. 5 illustrates a comparison of serum immunoglobulin titers in immunized sera separately measured against each component OMVs of bivalent OMV and heat-killed (HK) formulations.

The present subject matter relates to a novel formulation comprised of isolated outer membrane vesicles from two thyphoidal Salmonella strains such as Salmonella typhi C-6953 and Salmonella paratyphi A C-6915.

In the said formulations, two Salmonella strains are mixed in 1:1 ratio i.e. 50% of Salmonella typhi C-6953 and 50% of Salmonella paratyphi A-6915.

The immunogenicity and protective efficacy have been studied on adult mice after oral immunization with the said formulation.

The evaluation of the generation of humoral as well as cell mediated immune response after oral immunization by measuring different immunologic markers as well as anti-Vi polysaccharide specific serum immunoglobulin and Th1/Th17 specific cytokine response from splenic and DCs (Dendritic Cells) were performed.

This bivalent OMVs based vaccine could be an ideal human vaccine candidate against enteric fever.

The strains which are used in the said formulation are clinical isolates and thus do not have any modification or induced mutation in them.

Mutating a specific gene for over-expression of protective antigen may reduce immune-dominant non-protective antigen by mutating or deleting it. Moreover, LPS mutants might have some adverse effects on the end product; i.e., secreted OMVs. Mutating a gene also changes the bacterial genetic make-up and might eventually produce a specific type of protein which is not needed. Many other useful proteins could be lost in the process.

But, the said formulation does not change the genetic make-up of the microorganism and hence no such unwanted protein is produced.

No stress has been induced on the cultured bacteria in the form of antibiotics or using minimal medium, which eventually increases the cost-effectiveness of the final product.

Further, the said formulation does not incorporate antibiotics in it. Thus, reducing the chance of spreading antimicrobial resistance.

Unlike conventional practice, the present invention does not add any protein from outside or any other excipients such as lactose, sucrose, gelatin, sorbitol, human serum albumin and hence it is free from post-isolation purification steps.

From the analysis of the consortium, it has found that the consortium also comprises substantially high number of outer, inner, periplasmic and cytoplasmic protein, which have not infused from outside but were found to be present naturally.

It also possesses high number of cytosolic proteins (even proteins like DNA polymerase III, helicase, primase).

Any mutant stains has not been used in the novel formulation, the instant invention only uses their native form to deliver their natural contents in the host's body.

Further, effective short duration of immunization schedule can be achieved by the novel formulation. The protection can stay for 3 to 6 months without any further booster doses than the regimen stated.

The process for preparing the novel consortium has used log-phase culture of bacteria to isolate OMVs thus increasing the amount of TTSS proteins which are more potent in nature as an immunogen.

Also, as per the present invention the OMVs contain Vi-polysaccharide of Salmonella typhi. The content of Vi-polysaccharide in the bivalent formulation has been measured. The presence of Vi-polysaccharide in vaccine constituents makes the vaccine more effective against Salmonella typhi infection because, Salmonella typhi is covered with Vi-polysaccharide, presence of anti-Vi antibiotics in the serum would certainly elevated the level of protection. Presence of paratyphi A OMVs enlarges its protective nature further against paratyphi A.

The detailed result has given below:

Hypothetical proteins found after MALDI-TOF/TOF of Salmonella typhi C-6953 OMV:

| Sequence of amino acids | Hypothetical proteins found after protein BLAST |
|---|---|
| IITNVFLNAK | Permease |
| LTASLLLIYAK | Paraquat-inducible protein B |
| YEKNWFLPIVTIGK | Paraquat-inducible protein B |
| MLTASLLLIYAKNNGITLLVTK | Permease |
| DDLLSRINR | Hypothetical protein (Gammaproteobacteria) |

-continued

| Sequence of amino acids | Hypothetical proteins found after protein BLAST |
|---|---|
| GFSVPTPIQR | rRNA (cytidine-2'-O)-methyltransferase |
| GFSVPTPIQRK | Conjugal transfer protein TraB |
| FKPQETIFELGPKGK | Uncharacterised protein |
| IQEILVGITFLIAIAFIVK | Aminopeptidase N |
| IQEILVGITFLIAIAFIVKK | Aminopeptidase N |
| MIQEILVGITFLIAIAFIVK | Endonuclease |
| MLLALARLK | MFS transporter |
| PNILPTLPTLR | Respiratory nitrate reductase subunit |
| MPNILPTLPTLR | C4-dicarboxylate ABC transporter |
| PNILPTLPTLRILPTLPILR | DNA polymerase III subunit beta |
| VLVIGDLR | Two-component system response regulator GlrR |
| VDKGIVSLDR | DNA primase |
| MYRLLLGDGK | Phosphatidylserine/phosphatidylglycerophosphate/cardiolipin synthase |
| LVIQGFVKGVMHWVVEGGK | Glutaminyl-tRNA synthetase |
| ETPIQEEVKPLIEDILRTK | ATP-dependent metalloprotease |
| MVEIAAVRGR | 2,3-bisphosphoglycerate-independent phosphoglycerate mutase |
| VMELAKAALR | Enoyl-[acyl-carrier-protein] reductase |
| ETIEAALAQR | Transgylcosylase |
| DDIEARAIAK | Phase repressor protein |
| QIEAAKPK | Integrase |
| ILTVGKYPLMTL | tRNA pseudouridine synthase |
| LLDGNGLYLYVPVSGK | Putative antibiotic transporter |
| KFFVTDK | Rod shape-determining protein (ZapE) |
| ESLTLETVLK | Phosphoenolpyurate carboxylase |
| EIETLLTVQAPR | Type II restriction enzyme (methylase subunit) |
| SEPLWRTLIGIR | Potassium-transporting atpase A chain |
| DKIYGILGLLNEK | Carboxy-S-adenosyl-L-methionine synthase CmoA |
| DGDTIAIIAGMGRAAILR | Dihydroxy-acid dehydratase |
| VPITYHGFLMHSRGTIHIR | Transcriptional regulator AsnC |
| GFAGVATPMIRDGDTIAIIAGMGR | Type II secretion system protein GspE |
| AFYMHLPAAGK | AbrB family transcriptional regulator |
| KLLTILNAMLR | Glycoside-pentoside-hexuronide family transporter |
| LLTILNAMLRK | Sugar transporter |
| MAALVVTWFNPVIKAFYMHLPAAGK | Asparaginyl-tRNA synthetase |
| IDWIASQIR | Phage tail protein |
| KIDWIASQIR | Phage tail protein |

-continued

| Sequence of amino acids | Hypothetical proteins found after protein BLAST |
|---|---|
| QLNDLLKIIFFNVIR | Glutamate/aspartate:protein symporter GltP |
| GIVDPDLR | Transposase |
| MVELLDLIR | Magnesium and cobalt efflux protein CorC |
| VASESRAVVLQVDSLLK | 30S ribosomal protein S1 |
| LLVTVALAFLLVLVMAIFSIRSVMR | Permease (ABC transporter) |
| LSASADLLRR | Enterobactin synthase subunit F |
| MLQSIFTALLGR | 3-dehydroquinate synthase |
| LQSIFTALLGRLSASADLLR | Enterobactin synthase subunit F |
| DDEILDLLR | Helicase |
| ENGIKTVVNK | Ig-like domain repeat protein |
| IITNVFLNAK | Permease (nucleoside permease) |
| LTASLLLIYAK | Permease (MFS transporter) |
| YEKNWFLPIVTIGK | Respiratory nitrate reductase subunit |
| MLTASLLLIYAKNNGITLLVTK | Permease |
| DGQDLVISVR | Ser/Thr protein phosphatase |
| IVAPTQRIDSR | Structural protein |
| QLLRDVSHELR | Two component system sensor histidine kinase cpxa |
| LQALIGSQRQLLR | Helicase Type III restriction |
| LPLAGPASRTSDDLASH | Isochorismate synthase EntC |
| APGQTAAGHGLGLAIARR | Two component system sensor histidine kinase |
| DDGPGVADEHLPQLSEPFFRAPGQ TAAGHGLGAI | Two component system sensor histidine kinase PhoR |
| YFDAARSYGR | Family 31 glycosidase |
| VGLSLSGPQQAAVLR | Secreted chitinase |
| GMAEAPQVYWTTR | Prepilin peptidase |
| PHTLGNSGPAGTSLGLGLAALGRP GYITLGRAGDMGPDR | No sequence matches found |
| AALLIMLYSGK | MFS transporter |
| NNMQQLAKPEK | ClpV1 family T6SS atpase |
| MEIAESIEATRQSVIR | Cyclic diguanylate phosphodiesterase (EAL) domain-containing protein |
| MFQVLERAALLIMLYSGK | Isochorismatase |
| NNMQQLAKPEKVYLDNMNLMYA LSSSADIGNIR | No sequence matches found |
| TLLDGDLQHRIR | Peptide transporter |
| ATNNLAATTEAVAAGADR | Cytosol nonspecific dipeptidase |
| DPLGGPGKPVWAEVVSVWAK | Oxidoreductase |
| DPLGGPGKPVWAEVVSVWAKATN NLAATTEAVAAGADR | No sequence matches found |
| LGVSVATIER | Transcriptional regulator GalR |

-continued

| Sequence of amino acids | Hypothetical proteins found after protein BLAST |
|---|---|
| AVLIEAIEQIDR | Inner membrane protein |
| LTYPEIALRLGVSVATIER | LysR family transcriptional regulator |
| LPSRADAEDVTSETFAQVVENK | 2-aminoethylphosphonate ABC transporter permease subunit |
| AYLQSLMLMPEASVLSPEERAVLI EAIEQIDR | No sequence matches found |
| ETLEGVINAR | T3SS lipoprotein SsaJ |
| ETLEGVINARAK | EscJ/YscJ/HrcJ family type III secretion inner membrane ring protein |
| LMVVVERYPELK | Transcriptional regulator |
| GIVDPDLR | N-acetyl-D-glucosamine kinase |
| MVELLDLIR | Magnesium and cobalt efflux protein CorC |
| VSRGIVALSNGMNALAK | DNA-binding protein |
| LLVTVALAFLLVLVMAIFSIRSVMR | Amino acid ABC transporter permease |
| ILSTTVPVYGR | Tow-component sensor histidine kinase |
| QGVFKMSYHIR | Nucleoside-specific channel-forming protein Tsx |
| RIAYDVHGQALYAISR | Periplasmic-glucosidase |
| IVEFFEKNFPGITPDLIPTDNLQK | ABC transporter ATP-binding protein |
| DNLSLSYAMQQKELPDTQAIVED YLEQYTK | No sequence matches found |
| HTVTALSR | Hypothetical protein methyl-accepting chemotaxis protein) |
| VAIVGAGGTVGSFLAAALLKTGK | Sulfate transporter permease CysW |
| AGVPYIMPNGYAGDIEHVKFGQD VMLGPVAQANR | No sequence matches found |
| MFAETVIGAPHGILVSR | Pathogenicity island 2 effector protein SseC |
| FAETVIGAPHGILVSRITVYLSNAK | Inner membrane protein |
| MFAETVIGAPHGILVSRITVYLSNAK | Inner membrane protein (GntR/RmiB protein) |
| IQEILVGITFLIAIAFIVK | Aminopeptidase N |
| RGQPALSR | Cell division protein FtsN |
| GQPALSRR | Aaerobic dimethyl sulfoxide reductase subunit A |
| CRLQQATLTD | Paraquat-inducible protein PqiB |
| LVITLRDYGR | Arginine decarboxylase |

Hypothetical proteins present after MALDI-TOF/TOF of *Salmonella paratyphi* A C-6915 OMV:

| Sequence of amino acids | Hypothetical proteins found after protein BLAST |
|---|---|
| LDCTEGLDYCCICCPK | Transposon tn21 modulator protein (putative) |
| MIGHCKLDCTEGLDYCICCPK | Metal-dependent hydrolase or AMP nucleosidase |

-continued

| Sequence of amino acids | Hypothetical proteins found after protein BLAST |
|---|---|
| WQHLINDLQNDRSVDDEPGTYR | Phosphotriesterase or ABC transporter substrate-binding protein |
| MSEQLHGNMHYLLTSETYNGILVR | Fumarate hydratase FumA |
| MDEWMDGRQSLAEETSM | Sugar ABC transporter ATP-binding protein |
| ILALYCVTVMEAHEIVGVEWGMNR | Enterohemolysin |
| LLLIAHK | EscV/YscV/HrcV family type III secretion system export apparatus protein |
| HNSTSSTTPNQREGGPLSGIEFLSFGK | Virulense factor SrfB |
| TAGQLINWGMPTLAAEMLNALDCQR | Quinolinate synthase |
| IAVSWAMPVVLTQYDSVMATVMGDS | ATP-dependent helicase |
| IKEANEALIDAHNTQTGMLTEEAR | Molecular chaperone DnaJ |
| EANELSMQQTMMLIMNAGNAKAFAK | Hypothetical protein IT63_07870 or hypothetical protein SSPA0931 or hypothetical protein GZSPA_0913 |
| LWYCMMFGVTVATIYGAALILMV | Nicotinamide riboside transporter PnuC |
| GDPSAAVTIADIAMRAHDAGDLPEGIEGG | Oxidative stress defense protein (L-idonate 5-dehydrogenase |
| MDIMINASFLPHTDPEASLAFYR | NADH-quinone oxidoreductase subunit K |
| VQASGAEVMQEPTDQPWGARDCAFR | Molybdopterin molybdenumtransferase MoeA |
| YRSAPQAASAGSPTSPPASMQPTPSTSAS | Sodium:solute symporter family protein |
| ELRNSFIMDQDNQAAFINTHYK | Endonuclease or Guanosine moniphosphate reductase |
| SLHEDTIDPIENEADHLFIIRNSK | UDP-4-amino-4-deoxy-L-arabinose-oxoglutarate aminotransferase |
| DNVQCAPSGKAAITVSFVLEMDFR | Putative hydrolase./ -hydrolase fold |
| MNSRPPFPSTSSPPSQPSPYRYLGR | Aspartate racemase |
| QRAGAGNGETGASGVGEQQANFLFNLK | Fimbrial protein SthA |
| THEEAYAAAVEEFEANPPQVQRGK | SecY/SecA suppressor protein |
| GKKPLKPYEGDMPFFDNGDGTTTFK | Putative glycosyltransferase |
| LICKASSAQGCSPSTTLNQNFMQK | TrkH family potassium uptake protein |
| ASSAQGCPSTTLNQNFMQKGILECR | Flagellar hook protein FlgE |
| ALLGKMER | Cell division protein ZapB |
| FFRGSSQQSSGNPATDFFTVASPLPAAN | Outer membrane usher protein |
| HICFEIESYMFRIAFHDFFLPS | Maltose ABC transporter perrnease MalF |
| MILLHKYSIPACSCFQNIYALNTK | L-serine dehydratase 1 |
| MACVVSHQENQDCASLTPETFLPR | Formate dehydrogenase-H ferredoxin subunit |

-continued

| Sequence of amino acids | Hypothetical proteins found after protein BLAST |
|---|---|
| VEAARSER | Succinyl-diaminopimelate desuccinylase |
| MACSEQEGVGSPDEEALFASQEGVK | Tyrosine recombinase XerC |
| NLCTQPDGGYLTDEGIQMAER | ImpE family protein |
| VDGYTVVWDPETDMVVWAGGR | TonB-dependent receptor |
| MRIPSTGR | Lytic transglycosylase |
| LAVSAVVLLAALSVQGVR | Glu/Asp proton symporter GltP |
| MEPSNVLK | Pathogenicity island 2 effector protein SseD |
| VIAEQEGADSFVCQLAAWLHDLADDK | DedA family protein or putative membrane protein |
| MGHMERSFVSEDWAGLASWR | Molybdate ABC transporter permease |
| SFVSEDWAGLASWRCTCTDVDLGLR | Hypothetical protein (MdtB) |
| MAPWERK | Membrane protein (Permease) |
| NALFTPVR | ABC transporter substrate-binding protein |
| QMTAGMADIMGTSGLAWHQWK | Flagellar rod assembly protein/muramidase FlgJ or L-fuculokinase |
| MITQRLR | Cysteine/(glutathione ABC transporter ATP-binding protein/permease CydC |
| MPLAEGVTGEGRDTQSRPVGDDLDLTR | Glycerate 2-kinase |
| KILTEDYVNLVK | DNA topoisonterase IV subunit B |
| SQLNFYDTSVYNFIKSLDYAEVER | Helicase or Transcriptional repressor RbsR |
| NQCNILR | CRISPR-associated helicase/endonuciease Cas3 |
| MLFFYQLPFIIPIPSMQGNTFSR | Flagellar brake protein |

Bacterial Strains and Culture Conditions

OMV antigens were prepared from S. typhi C-6953 and S. paratyphi A C-6915, and S. typhi C-6.946 and S. paratyphi A BCR 148 for challenge study were collected from National Institute of Cholera and Enteric Diseases (NICED) culture bank. All strains were kept in 20% glycerol in brain heart infusion broth (Difco, USA) at 80° C. Prior to experimentation, each strain was grown in Tryptic Soy Broth (TSB; Difco, USA) at 37° C. under shaking conditions (100 rpm) or on plates in Tryptic Soy Agar (TSA; Difco, USA).

Preparation of OMVs

OMVs were prepared from two Salmonella enterica strains with slight modifications where cells were grown at 37° C. under shaking condition followed by centrifugation at 8000 rpm for 40 minutes at 4° C. Following filtration by 0.22 µm bacterial filters (Millipore, USA), OMVs were subsequently purified by ultracentrifugation (4 h, 140,000×g, 4° C.) using a Sorvall T-865 rotor, and re-suspended in Phosphate-Buffered Saline (PBS, pH 7.4). The protein concentration was determined by the modified Lowry protein assay kit (Pierce, USA). LPS O—Ag concentration was determined by a method used by Dubois et al.

FIG. 1 illustrates electron micrograph of OMVs attached to bacteria and isolated OMVs and characterization of isolated OMVs. A. i. OMVs attached to S. typhi bacteria and A. ii. Isolated OMVs from S. typhi. B. i. OMVs attached to S. paratyphi A and B. ii. Isolated OMVs from S. paratyphi A.

FIG. 1a illustrates C. Size of isolated OMVs. S. typhi OMVs were found to be much larger than that of the S. paratyphi A OMVs.

Negative Staining of OMVs and OMV-Secreting Bacteria

A 5 µl aliquot of secreted OMVs were placed on a carbon coated grid and left for 1 minute for proper absorption. The grid was then washed with two drops of Tris-HCl buffer. After blotting excess fluid, the sample was stained with 2% aqueous solution of uranyl acetate. In case of negative staining of bacteria-secreting OMVs, the same procedure was followed with log-phase live bacterial cells. Both the negatively stained OMVs and bacteria-secreting OMVs were observed under Tecnai 12 (as given in FIG. 1).

FIG. 2a illustrates BALB/c mice were immunized by oral gavage on day 0 and then two subsequent booster doses follow as stated. Mice were challenged on day 35 via an intra-peritoneal challenge model.

From FIG. 2b, the immunization and challenge regimen in mice can be understood clearly. Mice were immunized on days 0, 14 and 28 and challenged on 35th days after 1st immunization. Blood were collected from on indicated days.

The experiments which have performed are given below:

Animals

Seven weeks old, BALB/c mice of either sex were taken from the animal resource division of NICED, Kolkata. Male and female mice were caged separately groups of 10 and maintained at a temperature of 25° C. with humidity at 75%. Mice were fed sterile food and water. All the animal experiments were conducted following the standard operating procedure as outlined by Committee for the Purpose of Control and Supervision of Experiments on Animal (CPCSEA), Ministry of environment and forest, Government of India. The animal experimental protocol was approved by the Institutional Animal Ethical Committee of NICED with the project approval no. PRO/108 May, 2014-July, 2017. Oral Immunization 7 weeks old female BALB/c mice were kept empty stomach 24 hours before the immunization date, water adlibitum. Mice were immunized orally on days $0^{th}$, $14^{th}$ and $28^{th}$ (FIG. 2) with 25 μg of purified S. typhi and S. paratyphi A OMVs (1:1) in 200 μL of PBS following the protocol as explained previously.

Collection of Serum and Stool

Blood was collected from the lateral tail vein at different time intervals on the 0th, 14th, 21st, 28th, 35th, 78th, 90th day of first oral immunization. The collected blood was taken in BD Microtainer (BD, NJ, USA) followed by centrifugation (1000 rpm, 10 min and 4° C.). Stools from immunized and non-immunized mice were collected in an aseptic Eppendorf by pressing the abdominal region. Stools were then homogenized by a plastic homogenizer and centrifuged at 10000×g for 10 min to remove the debris. The supernatant was collected and stored.

The results of representative immunoblot analysis against OMVs, from two typhoidal strains are given in FIG. 3.A. SDS-PAGE profile of OMVs extracted from two strains of typhoidal salmonellae. Lane M: Low molecular weight marker (Bangalore GeNei), Lane 1: S. typhi, Lane 2: S. paratyphi A.B. Immunoblot against each component of the OMVs of the bivalent formulation probed with $28^{th}$ days anti-bivalent OMVs serum from mice. Lane M: Pre-stained molecular weight marker (Bangalore Genei), Lane 1: S. typhi, Lane 2: S. paratyphi A OMV.

SDS-PAGE and Immunoblot

The protein content of the OMVs recovered from Salmonella strains were determined as described earlier in this paper. 80 μg of proteins were boiled in 5×SDS-PAGE buffer and loaded onto a 12% SDS-PAGE gel. The gel was then stained by either Coomassie or silver stain. For immunoblot assay, gel was transferred onto nitrocellulose membrane (Bio-Rad, USA) by using the ATTO AE-6687 (Japan) blot apparatus. The polyclonal antibody rose in mice and HRP-conjugated rabbit anti-mouse secondary IgG were used to detect the proteins which were immunogenic.

FIG. 4 illustrates dot blot analysis against extracted LPS from two typhoidal strains. Lane 1: S. typhi LPS, Lane 2: S. paratyphi A LPS.

Here, 1, 2, and 3 denotes three different concentrations of LPSs against which the dot blot analysis was performed.

Dot Blot Assay.

Dot blot analysis was done as described previously. Briefly, LPS of the two strains were taken and blotted onto a nitrocellulose membrane. The membrane was then washed with Tris-Buffered Saline (TBS) contains 0.1% Tween-20. The membrane was then incubated with primary and secondary antibody successively, where OMV-immunized mice serum was serving the purpose of a primary antibody and the blot was then finally developed by chemiluminescence.

ELISA

Different immunoglobulins; e.g. IgG and its sub-types (IgG1, IgG2a, IgG3), and IgA, sIgA and IgM were measured by ELISA as stated by Keren (23). Briefly, disposable polystyrene micro-titer wells (Nunc, Denmark) were separately coated with OMVs (5 μg/well) from either strains of the immunogens (Table 1) and incubated for 18 h at 4 C. Wells were washed and blocked with Bovine Serum Albumin (BSA; Sigma Chemical, USA). After washing the wells with PBS-T (PBS with 0.5% Tween-20, Sigma Chemicals, USA) and incubated with serially diluted serum samples, 100 μL HRP conjugated goat anti-mouse immunoglobulin was added and incubated. After washing with PBS, the substrate o-phenyl-Di-amine (OPD) was added to each well followed by stopping the reaction after 10 min by adding 100 μL of 2 N sulphuric acid. OD492 was taken. The experiments were repeated three times for each immunoglobulin, with the immunized and non-immunized serum, collected from individual mice, before, during and after immunization. The same procedure was carried out when ELISA were done against Vi-polysaccharide of S. typhi.

A serum immunoglobulin titer in immunized sera were separately measured against each component OMVs of bivalent OMV and heat-killed (HK) formulations. A. Serum IgG (i), IgG1 (ii), IgG2a (iii), IgG3 (iv); B. Serum IgA; C. Serum IgM response against each of the two OMVs and heat-killed immunogens at pre-immunization, immunization and postimmunization. The horizontal axis indicates the days of blood collection. Data represented here are the mean values+/− Standard Deviation (SD) of three independent experiments. The differences in post-immunization day wise response of each of the studied antibodies against each of the two OMVs were highly significant (P value<0.005) (shown in FIG. 5).

Figure 5A:
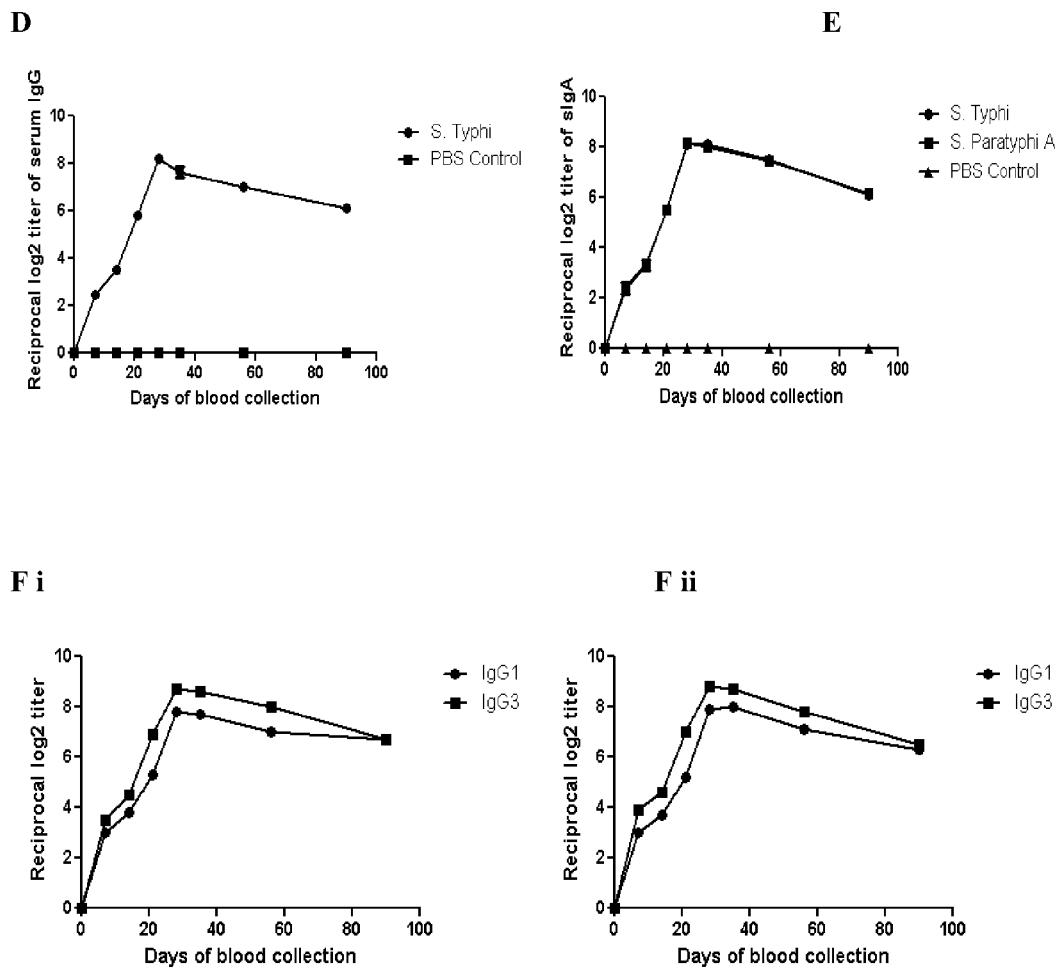
FIG. 5a illustrates serum immunoglobulin titers in immunized sera separately measured against each component OMVs of bivalent OMV formulation.

FIG. 5a illustrates anti-Vi serum IgG; E. Secretory IgA; F. i. ii. Serum IgG1 and IgG3 response against each of the two OMVs, Salmonella typhi and paratyphi A, respectively at pre-immunization, immunization and post-immunization periods. The high serum IgG3 titer against serum IgG1 titer indicates higher Th1 cell-mediated immune response in adult mice sera after three doses of immunization. The horizontal axis indicates the days of blood collection. Data represented here are the mean values+/− Standard Deviation (SD) of three independent experiments. The differences in post-immunization day wise response of each of the studied antibodies against each of the two OMVs were highly significant (P value<0.005).

Ex Vivo Studies on Isolated Dendritic Cells

Dendritic cells from bone marrow of non-immunized BALB/c mice were cultured for 7 days in complete RPMI containing 10% FBS in the presence of 20 ng/ml GM-CSF (Tonbo). Cells were then treated with 100 ng/ml bivalent OMV and incubated in 37° C. for 24 hours in presence of 5% CO2. Different cytokines, namely IFN-γ, IL-4, IL-12p70, IL-1β and IL-23 were then measured (refer FIG. 6 A) by cytokine ELISA kit.

Splenocyte Re-Stimulation Assay.

After 2 weeks from the end of last immunization, splenic cells from immunized BALB/c mice were cultured for 2 hours in complete RPMI containing 10% FBS. Cells were then treated with 100 ng/ml bivalent OMV and incubated in 37 C for 24 hours in presence of 5% CO2. Different cytokines, namely IFN-γ, IL-6 and IL-17 were then measured (FIG. 6 B) by cytokine ELISA kit (Invitrogen, USA) (8).

Figure 7:
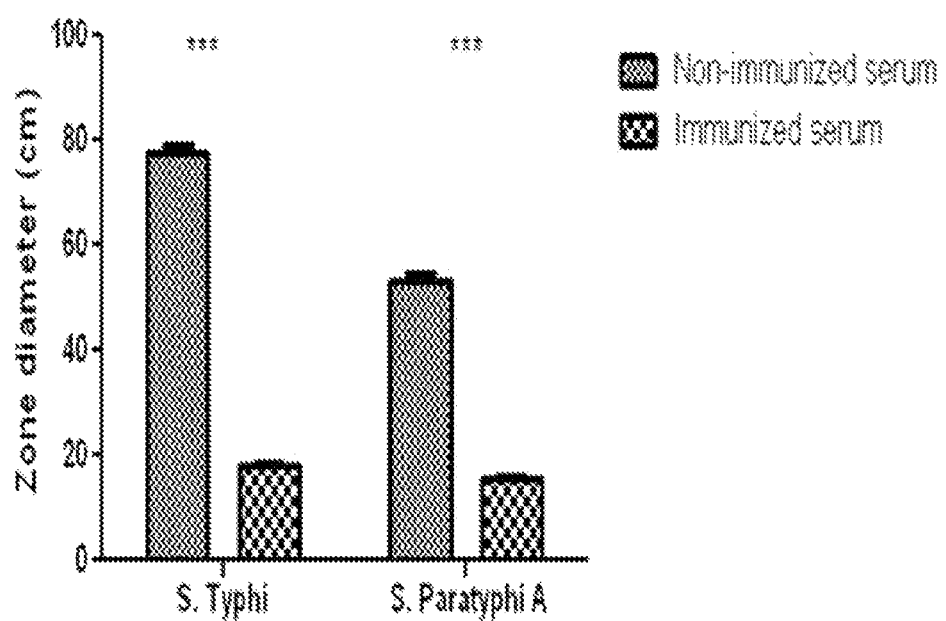
FIG. 7 illustrates Serum from bivalent immunized mice inhibits S. typhi and S. paratyphi A motility.

FIG. 7 illustrates serum from bivalent immunized mice inhibits S. typhi and S. paratyphi A motility.

Motility Assay

Motility assay was done as previously described, with modifications. Briefly, the immunized and non-immunized serum samples were mixed with PBS at a concentration of 1:400 and poured on soft agar (0.3%) plates. The plates were kept for an hour to get the serum mixed PBS soak in the plate. After the plates became dry, log-phase bacteria (OD600=0.8) were pricked in the middle of the plate. The plates were then incubated at 37° C. for 24 hours. After 24 hours, the results were seen as in FIG. 7.

Figure 8:
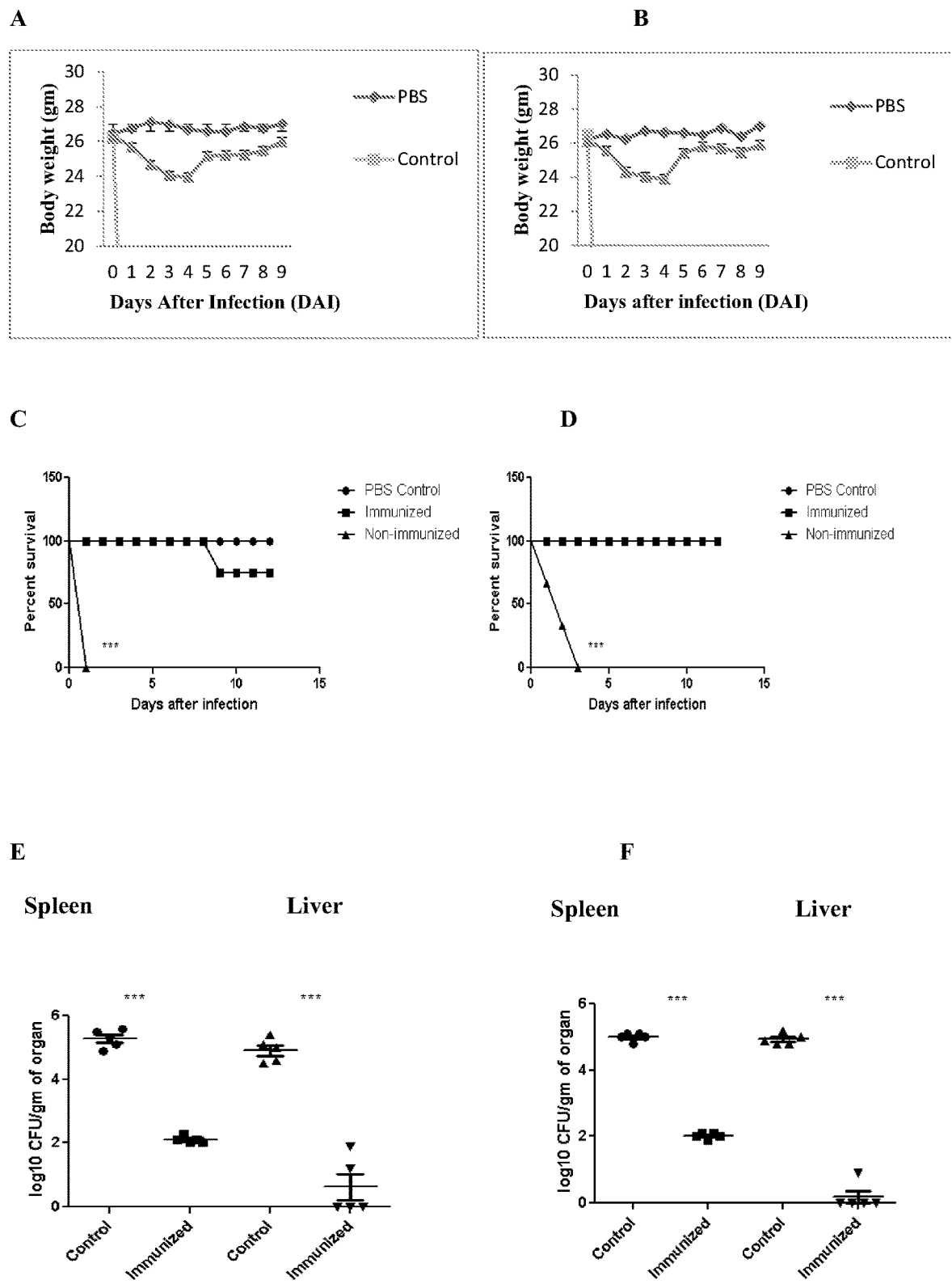
FIG. 8 illustrates immunization with the bivalent OMVs provides protection in adult mice model.

FIG. 8 illustrates an Immunization with the bivalent OMVs provides protection in adult mice model. Mice were immunized with 1:1 mixture of typhoidal OMVs using 25 μg total OMVs per dose and a three-dose immunization. Mice were then challenged with $1\times10^6$ CFU/ml of each challenge strains intra-peritoneally and observed for the period of survival for 12 days. A., B. Body weight was measured for each mouse until $9^{th}$ day post-infection and C., D. percent survival was calculated. E., F. Mice were further challenged with $2\times10^8$ CFU/ml heterologous strains of challenge bacteria and the systemic infection of the bacteria in these mice were determined by serial dilution of the spleen and liver. Bivalent S. typhi and S. paratyphi A OMV Protect Adult Mice From S. typhi and S. paratyphi A Challenge After four successive oral immunizations with bivalent OMVs formulation, protective efficacy was observed in an adult mice intra-peritoneal model (FIG. 8). At 9 DPI (Days Post Infection), it was observed that $1\times10^5$ $1\times10^6$ CFU/gm of spleen in non-immunized mice, whereas, $2\times10^2$ CFU/gm of spleen was the highest colonization found in immunized mice's spleens.

Tissue homogenates from liver reveals only 10-100 organisms/gm in case of immunized mice, whereas, in non-immunized mice, 5-log fold higher colonization ability was observed.

Both immunized and non-immunized mice were challenged with $2\times10^6$ CFU/ml intra-peritoneally and kept them for 12 days for survival assay. In case of non-immunized mice, all the mice died within 1 4 days. But, 80% and 100% immunized mice were still alive. This result suggests that, our bivalent formulation is inhibiting the systemic infection of typhoidal salmonellae in mice and it indeed protecting the mice from lethal infection.

In the majority of cases, the data presented are not normally distributed due to biological variation. Therefore, non-parametric tests were used for all data analysis. Comparison between two categorical variables was made using the two-tailed student's test.

Comparison between multiple categorical variables was made using the one-tailed student's test. Each experiment was repeated at least three times. A P value of <0.05 or <0.01 were considered significant GraphPad Prism 5 for Windows OS was used for all statistical analyses.

The effectiveness of both Salmonella typhi and paratyphi A OMVs have been studied through various experiments.

When the mice were immunized with Salmonella typhi OMVs, they were protected from Salmonella typhi infection (evaluated from the bacterial count from spleen and liver 3 days' post infection). But when the same Salmonella typhi OMVs-immunized mice were challenged with Salmonella paratyphi A, very less amount of protection was found. The same trend was seen when monovalent Salmonella paratyphi A OMVs is used to immunize mice. They were protected from Salmonella paratyphi A infection, but not protected from Salmonella typhi infection. The results are following:

FIG. 9 illustrates the first panel shows colonization of Salmonella typhi clinical isolate in Salmonella typhi OMV-immunized mice. On the other hand, the second panel shows colonization of Salmonella paratyphi A clinical isolate in Salmonella typhi OMV-immunized mice. At least 2 fold more colonization was seen when Salmonella typhi OMV-immunized mice were challenged with Salmonella paratyphi A rather than Salmonella typhi clinical isolate. Homologous protection was seen, but no heterologous or cross-protection was observed.

FIG. 10 illustrates the first panel shows colonization of Salmonella typhi clinical isolate in Salmonella paratyphi A OMV-immunized mice. On the other hand, the second panel shows colonization of Salmonella paratyphi A clinical isolate in Salmonella paratyphi A OMV-immunized mice. At least 2 fold more colonization was seen when Salmonella paratyphi A OMV-immunized mice were challenged with Salmonella typhi rather than Salmonella paratyphi A clinical isolate. Homologous protection was seen, but no heterologous or cross-protection was observed in this case also.

Figure 11:
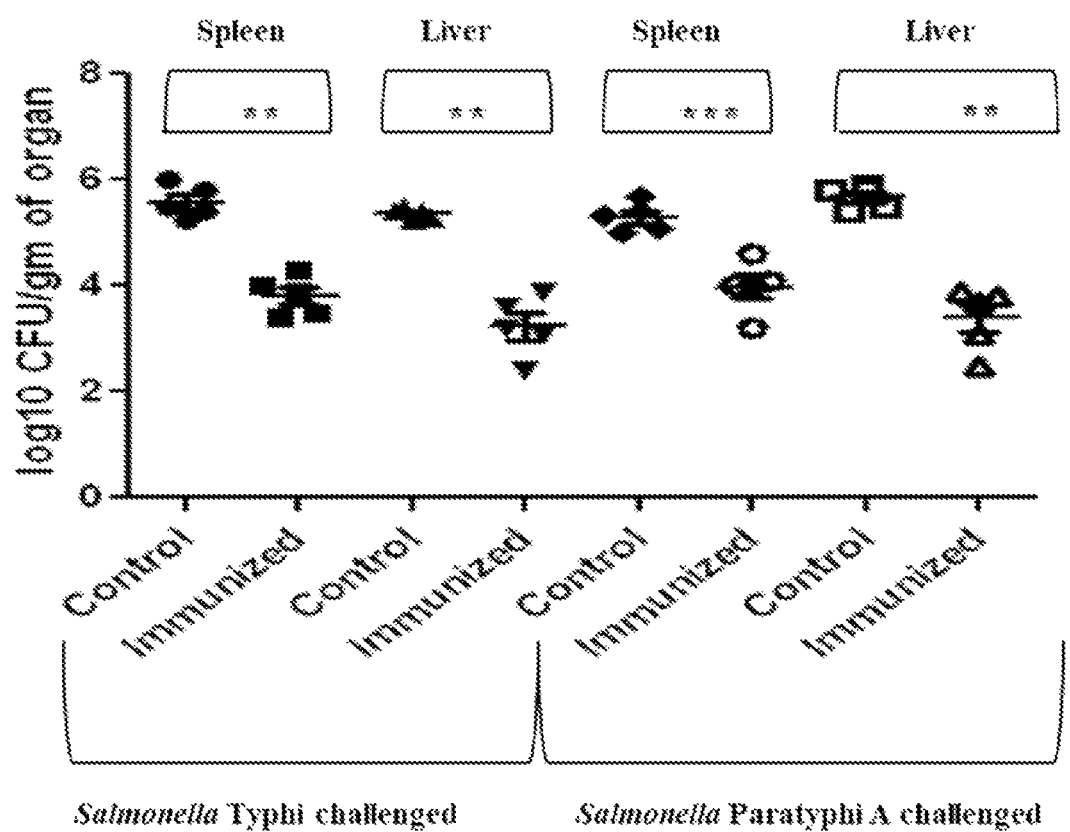
FIG. 11 illustrates the assessment of the effect of OMVs isolated from 24-hours culture.

The effect of OMVs isolated from 24 hours' culture was assessed. Although this result shows that the immunized mice are significantly protected from the challenge, but the level of protection is much higher in case of OMVs isolated from 5 hours' culture (refer to Patent application FIG. 8. E, F) (as shown in FIG. 11).

Figure 12A:
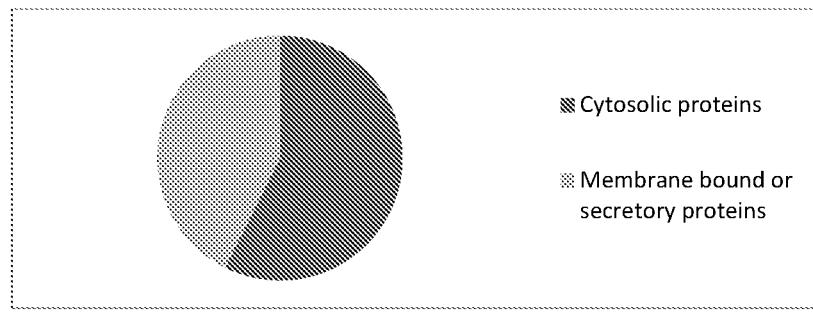
FIG. 12a illustrates classification of Salmonella typhi OMV-associated proteins based on their location of appearance in the bacteria.
Figure 12B:
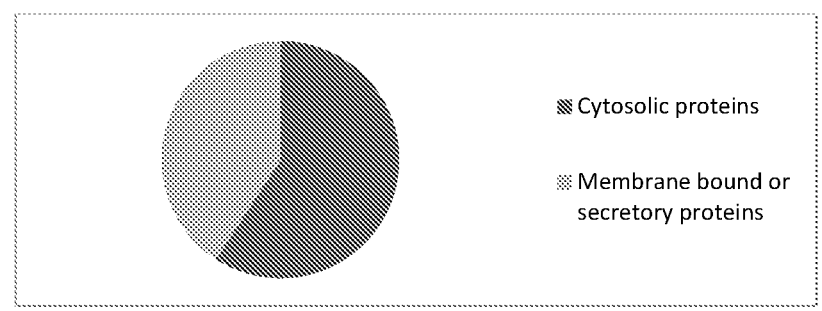
FIG. 12b illustrates classification of Salmonella parathyphi A OMV-associated proteins based on their position in the bacteria.
Figure 12C:
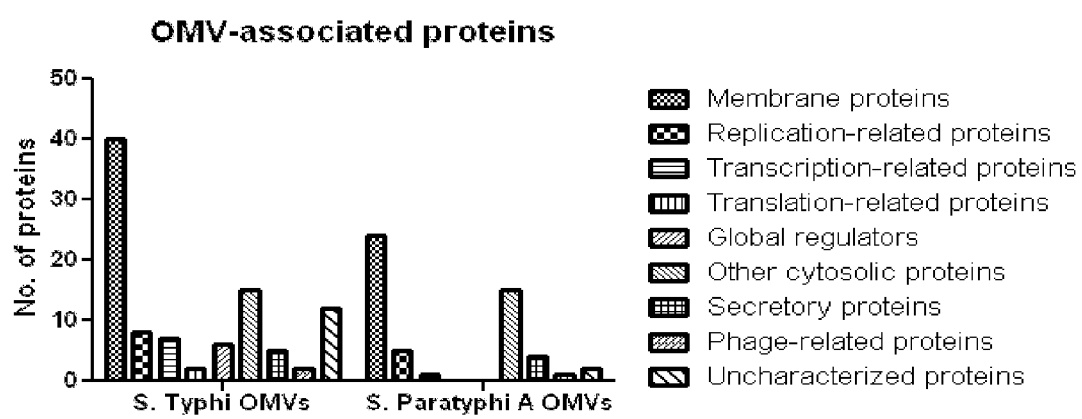
FIG. 12C illustrates OMV associated protein.
Figure 13:
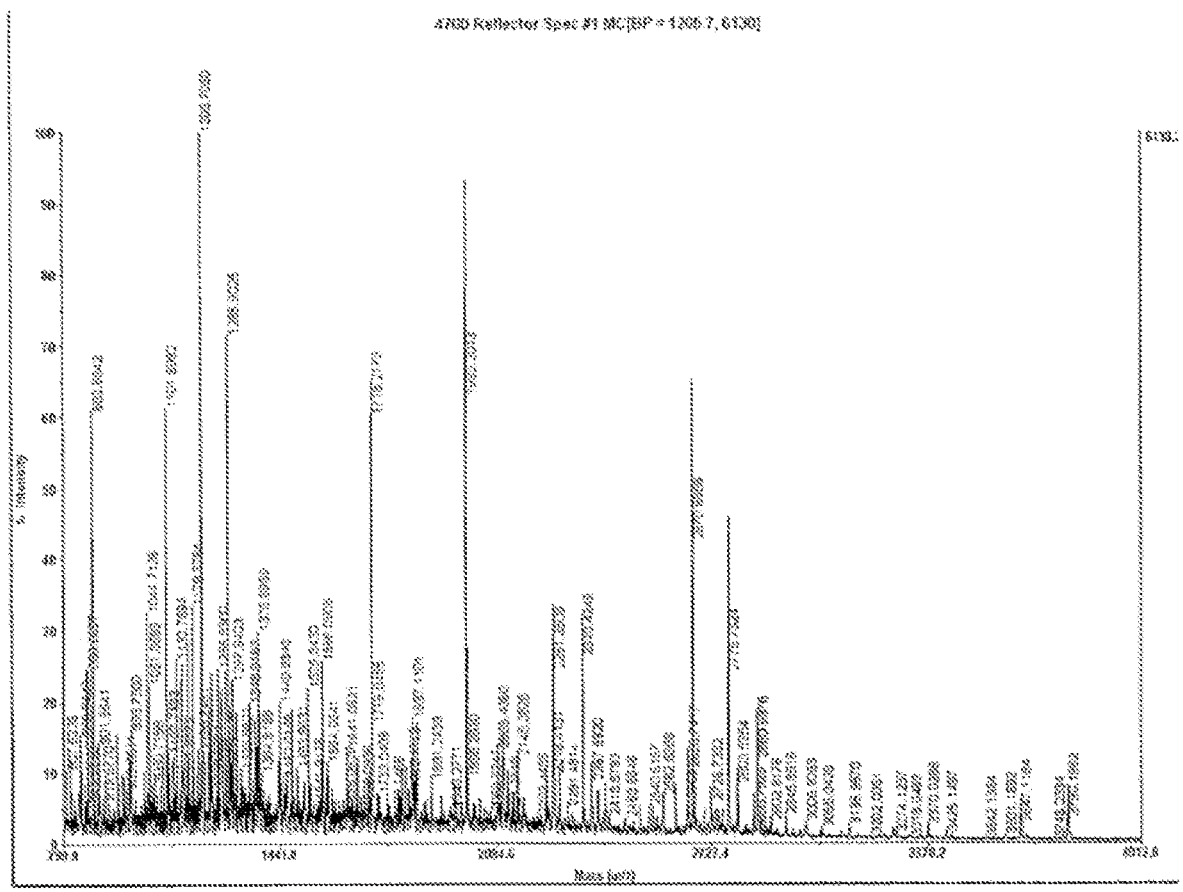
FIG. 13 illustrates MALDI-TOF/TOF mass spectrometry spectrum of Salmonella typhi C-6953 OMV.
Figure 14:
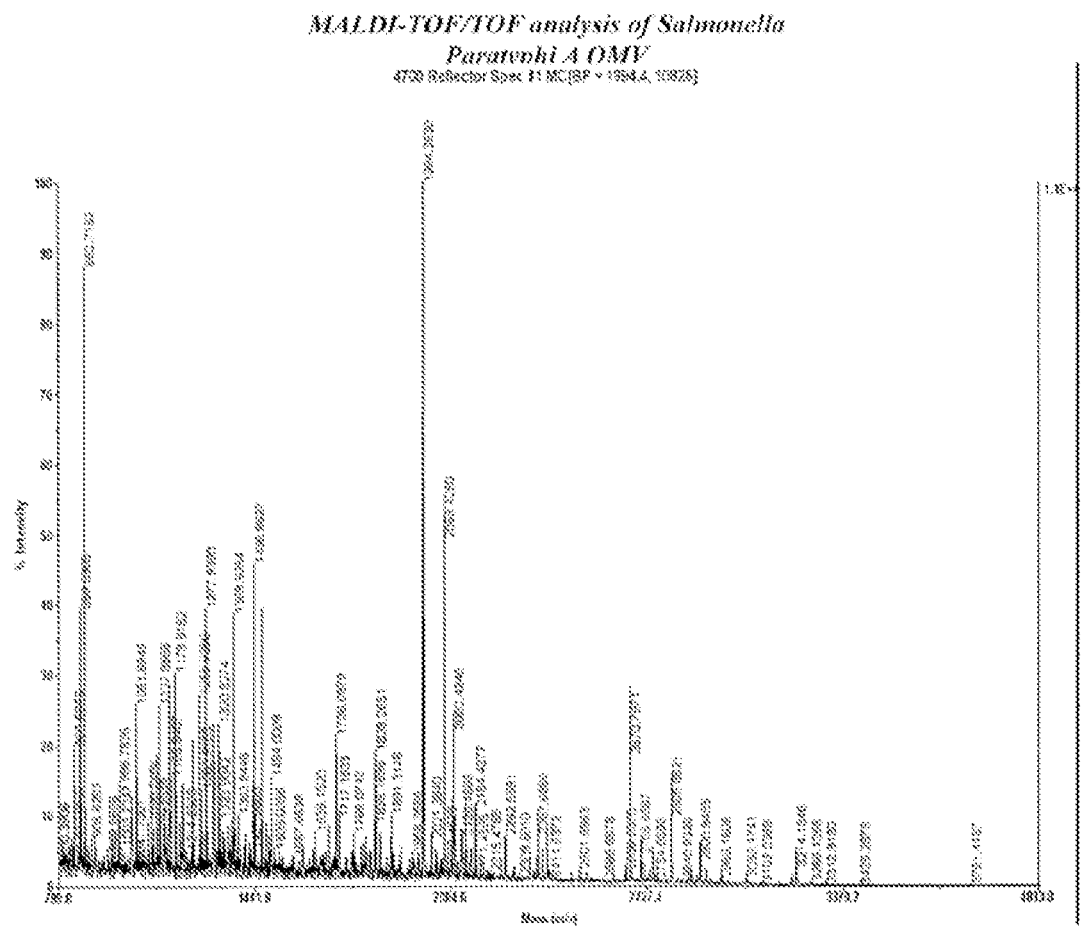
FIG. 14 illustrates MALDI-TOF/TOF mass spectrometry spectrum of Salmonella paratyphi A C 6915 OMV.

The OMVs from log-phase culture bacteria caused much less colonization in spleen and liver and substantially much more effective them any other formulations. It is rich in many proteins which were reported to be secreting via OMVs until recently (FIG. 12).

The OMVs of two strains of bacteria as claimed contains proteins of different sizes as well as LPS in them. Western blot analysis indicates the presence of strong immune response against the immunogens present in BOMVs. Dot blot analysis serves the purpose of proving this immunogen to be effective and immunogenic against LPS of these two strains. Three doses of oral immunization of these BOMVs formulation in mice induces a significant rise in the level of immunoglobulins specific for isolated OMVs. Presence of sIgA against OMVs formulation and IgG specific for Vi-polysaccharide of S. typhi shows the potency of our bivalent formulation against S. typhi infection.

As Vi-polysaccharide is the outer covering of S. typhi, immunoglobulins present against this component indicates the presence of Vi-polysaccharide in the BOMVs. Because of their intra-cellular nature, both S. typhi and S. paratyphi A can only be eradicated from the host in the presence of significant Th1 cell-mediated immune response along with humoral immune response. A Th1 biased immune response was seen in the ELISA data.

Also, a significant up-regulation in the level of IFN-γ, IL-6, IL-12p70, IL-1β and IL-23 from the isolated BMDCs and IFN-γ, IL-6 and IL-17 from splenocytes shows that the induced response was a result of mainly a Th1 and Th17 cell mediated immune response. Moreover, as verified by sera and splenocytes adoptive transfer experiments, the protective effect of BOMVs vaccination was dependent on both humoral and cellular immunity. So, both humoral as well as cellular arms of the host's immune system are being activated upon the exposure of BOMVs in mice. Our BOMVs immunized mice sera can also inhibit the motility of the wild type strains of typhoidal salmonellae. Inhibition of motility means the bacteria will no longer be able to find their receptors for binding on the human epithelium thus, rendering their inability to cause infection. MTT assay was done to check the reactogenicity of BOMVs. It was found BOMVs were less reactogenic than the conventional heat-killed and whole cell lysate immunogens.

Inhibition to cause infection in mice was further confirmed by anti-colonization and survival assays. In our anti-colonization assay, immunized mice were challenged with circulating strains of typhoidal salmonellae via the intra-peritoneal route. Significant increase in the level of survival in the BOMVs immunized group was seen. Also, the presence of typhoidal salmonellae in spleen and liver were found to be significantly less in immunized mice. Taken together, these findings suggested us that BOMVs could be used as a novel non-living human vaccine candidate against S. typhi and S. paratyphi A infections in future.

Statistical Analysis

In the majority of cases, the data presented are not normally distributed due to biological variation. Therefore, non-parametric tests were used for all data analysis. Comparison between two categorical variables was made using the two-tailed student's t test. Comparison between multiple categorical variables was made using the one-tailed student's t test. Each experiment was repeated at least three times. A P value of <0.05 or <0.01 were considered significant. GraphPad Prism 5 for Windows OS was used for all statistical analyses.

The Non-Limiting Advantages are Given Below:

- The consortium consists of OMVs (BOMVs) together as an immunogen and contain proteins of different sizes and LPS among other constituents.
- The said consortium induces significant immune response after three doses of oral immunization in mice. Western blot analysis assures their immunogenicity. Dot blot analysis shows the ability of induction of immunogenicity against LPS of circulating strains.
- Significant rise in the serum IgG, IgM, IgA, sIgA was seen after three doses of oral immunization. High level of serum IgG3 instead of serum IgG1 indicates a Th1-baised immune response. A high titer against the Vi-polysaccharide of S. typhi was seen. This indicates the induction of a humoral immune response in the mice.
- Treating the isolated BMDCs with the said consortium results in the elevation of Th1-biased cytokines. Rise in Th1 and Th17-baised cytokines were seen in isolated splenocytes from immunized mice. This indicates the induction of a strong Th1-cell mediated immunity in mice.
- The said consortium immunized mice sera can significantly inhibit the motility of wild type circulating strains of typhoidal salmonellae. Inhibition of motility renders the bacteria ineffective in the induction of its virulence.
- The said formulation is much less reactogenic than the conventional heat-killed and whole cell lysate immunogens.
- The formulation immunized mice were protected against wild type circulating strains of typhoidal salmonellae. The level of colonization in spleen and liver were also found to be significantly less than that of the non-immunized mice.

We claim:

1. A bivalent formulation for enteric fever, the bivalent formulation comprising outer membrane vesicles (OMVs) isolated from unmutated *Salmonella typhi* C-6953 and *Salmonella paratyphi* A C-6915, wherein *Salmonella typhi* C-6953 and *Salmonella paratyphi* A C-6915 OMVs are present in a ratio of 1:1, wherein the bivalent formulation is free of antibiotics, excipients, and protective proteins, and wherein the *Salmonella typhi* C-6953 and *Salmonella paratyphi* A C-6915 are cultured in absence of a minimal medium prior to the isolation of the OMVs.

2. The bivalent formulation claimed in claim 1, which further comprises outer, inner, periplasmic, cytoplasmic, and secretion system proteins.

3. The bivalent formulation as claimed in claim 1, which further comprises DNA polymerase III, helicase, and primase.

4. A method for preparing a bivalent formulation of claim 1 for a vaccine for treating enteric fever, the method comprising:

(i) growing *Salmonella typhi* C-6953 and *Salmonella paratyphi* A C-6915 cells separately at 37° C., under shaking condition followed by centrifugation;

(ii) filtering the bacterial cultures by 0.22 μm bacterial filtration units to obtain outer membrane vesicles (OMVs) and purifying OMVs through ultracentrifugation; and (iii) re-suspending the isolated OMVs in a phosphate-buffered saline at pH 7.4 to prepare the bivalent formulation, wherein *Salmonella typhi* C-6953 and *Salmonella paratyphi* A C-6915 OMVs are present mixed in a ratio of 1:1, wherein the bivalent formulation comprises unmutated proteins of *Salmonella typhi* C-6953 and *Salmonella paratyphi* A C C-6915, wherein the bivalent formulation is free of antibiotics, excipients, and protective proteins, and wherein the bivalent formulation is prepared in absence of a minimal medium.

5. The method of claim 4, wherein the centrifugation occurs at 8000 rpm for 40 min at 4° C.

6. The method of claim 4, wherein the ultracentrifugation occurs for 4 hours at 140,000×g at 4° C.

7. The bivalent formulation of claim 1, wherein *Salmonella typhi* C-6953 and *Salmonella paratyphi* A C-6915 are in log phase having an increased amount of TTSS (Type Three Secretion System) proteins and a low LPS content and wherein the proteins and low LPS present in the bivalent formulation is able to induce immunogenicity against *Salmonella typhi* C-6953 and *Salmonella paratyphi* A C-6915.

* * * * *